(12) United States Patent
Herradon García et al.

(10) Patent No.: US 7,932,266 B2
(45) Date of Patent: Apr. 26, 2011

(54) ISOQUINOLINE DERIVATIVES AS CALPAIN INHIBITORS

(75) Inventors: Bernardo Herradon García, Juan de la Cierva (ES); Roberto Chicharro Martin, Juan de la Cierva (ES); Vicente Jesús Aran Redo, Juan de la Cierva (ES); Mercedes Alonso Giner, Juan de la Cierva (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 796 days.

(21) Appl. No.: 11/793,011

(22) PCT Filed: Dec. 5, 2005

(86) PCT No.: PCT/ES2005/070171
§ 371 (c)(1),
(2), (4) Date: Dec. 19, 2007

(87) PCT Pub. No.: WO2006/064075
PCT Pub. Date: Jun. 22, 2006

(65) Prior Publication Data
US 2008/0090862 A1    Apr. 17, 2008

(30) Foreign Application Priority Data

Dec. 16, 2004 (ES) .................................. 200402995

(51) Int. Cl.
*A61K 31/44* (2006.01)
*C07D 217/24* (2006.01)
(52) U.S. Cl. .......... 514/308; 514/309; 546/140; 546/141
(58) Field of Classification Search ........................ None
See application file for complete search history.

(56) References Cited

U.S. PATENT DOCUMENTS

| 5,541,290 A | 7/1996 | Harbeson et al. |
| 5,576,435 A | 11/1996 | Melikian-Badalian et al. |
| 6,103,720 A | 8/2000 | Lubisch et al. |

FOREIGN PATENT DOCUMENTS

| EP | 1 743 883 | 1/2007 |
| ES | 200301125 | 5/2003 |
| ES | 200401104 | 5/2004 |
| WO | 96/41638 | 12/1996 |
| WO | 2004/101494 | 11/2004 |

OTHER PUBLICATIONS

Kevin K.W. Wang et al., "Development and Therapeutic Potential of Calpain Inhibitors", Adv. Pharmacol., vol. 37, pp. 117-152 (1996).
Shoji Hata et al., "Domain II of m-calpain is a $Ca^{2+}$-dependent cysteine protease", FEBS Letters, vol. 501, pp. 111-114 (2001).
Tatiana G. Sazontova et al. "Calpains: physiological and pathophysioloqical significance", Pathophysiology, vol. 6, pp. 91-102 (1999).
Swapan K. Ray et al., "Calpain in the pathophysiology of spinal cord injury: neuroprotection with calpain inhibitors", Brain Research Reviews, vol. 42, pp. 169-185 (2003).
Frank J.E. Vajda "Neuroprotection and neurodegenerative disease", Journal of Clinical Neuroscience, vol. 9(1), pp. 4-8 (2002).
Adam Doble, "The Role of Excitotoxicity in Neurodegenerative Disease: Implications for Therapy", Pharmacol. Ther., vol. 81, No. 3, pp. 163-221 (1999).
Paolo Calabresi et al. "Ionotropic glutamate receptors: still a target for neuroprotection in brain ischemia? Insights from in vitro studies", Neurobiology of Disease, vol. 12, pp. 82-88 (2003).
Ivy Carroll et al., "Pharmacological properties of JDTic: a novel K-opioid receptor antagonist", European Journal of Pharmacology, vol. 501, pp. 111-119 (2004).
Arnaud LeTiran et al., "Design and Evaluation of Affinity Labels of Functionalized Amino Acid Anticonvulsants", J. Med. Chem., vol. 45, pp. 4762-4773 (2002).
Geraldine C.B. Harriman et al., "Cell Adhesion Antagonists: Synthesis and Evaluation of a Novel Series of Phenylalanine Based Inhibitors", Bioorganic & Medical Chemistry Letters, vol. 10, pp. 1497-1499 (2000).
Yuanhui Huang et al., "The calpain family and human disease", TRENDS in Molecular Medicine, vol. 7, No. 8, pp. 355-362 (2001).
Ana Montero et al., "Studies on aromatic compounds: inhibition of calpain I by biphenyl derivatives and peptide-biphenyl hybrids", Bioorganic & Medical Chemistry Letters, vol. 14, pp. 2753-2757 (2004).
Ann Montero et al., Peptide-Biphenyl Hybrids as Calpain Inhibitors[1], Chemistry & Biodiversity, vol. 1, pp. 442-457 (2004).
Enrique Mann et al., "Novel Peptide-Heterocycle Hybrids: Synthesis and Preliminary Studies on Calpain Inhibition", Adv. Synth. Catal., vol. 344, No. 8, pp. 855-867 (2002).
Paul Lloyd-Williams et al., "Chemical Approaches to the Synthesis of Peptides and Proteins", New Directions in Organic and Biological Chemistry, CRC Press, Boca Raton (1997)—Table of Contents.
B.M. Frost et al., "Selectivity, Strategy and Efficiency in Modern Organic Chemistry", Comprehensive Organic Synthesis—Elsevier, http://www.elsevier.com/wps/find/bookdescription.cws_home/26507/...—Table of Contents, 2006.
Francisco Sánchez-Sancho et al., "Efficient Syntheses of Polyannular Heterocycles Featuring Microwave-Accelerated Bischler-Napieralski Reaction, Stereoselective Heck Cyclization, and Claisen Rearrangement", Synlett, No. 4, pp. 509-513 (2000).
Francisco Sánchez-Sancho et al., "Efficient Synthesis of Chiral Isoquinoline and Pyrido[1,2-b]-isoquinoline Derivatives via Intramolecular Heck Reactions", Adv. Synth. Catal., No. 4, pp. 360-368 (2001).

(Continued)

Primary Examiner — Zinna N Davis
(74) Attorney, Agent, or Firm — Wenderoth, Lind & Ponack, L.L.P.

(57) ABSTRACT

The invention relates to derivative compounds of partially-reduced isoquinoline with substitution of a sec-butyl group at position 3 with calpain inhibitor activity. The inventive compound comprises an ester or amide derived from (3-sec-butyl-1-oxo-2,3-dihydro-1H-isoquinolin-4-yliden)-acetic acid and (3-sec-butyl-1-thioxo-2, 3-dihydro-1H-isoquinolin-4-yliden)-acetic acid. Compounds having formula I or II can be used in the preventive or therapeutic treatment of a degenerative disease.

10 Claims, 1 Drawing Sheet

OTHER PUBLICATIONS

Patrick Metzner "*Thiocarbonyl Compounds as Specific Tools for Organic Synthesis*", Topics in Current Chemistry, vol. 204, pp. 127-181 (1999).

S. Scheibye et al., "*Studies on Organophosphorus Compounds XXI.* The Dimer of p-Methoxyphenylthionophosphine sulfide as Thiation Reagent. A New Route to Thiocarboxamides*", Bull. Soc. Chim. Belg., vol. 87/n°3 (1978).

Francisco Sánchez-Sancho et al., "*Short syntheses of (S)-pipecolic acid, (R)-coniine, and (S)-ō-coniceine using biocatalytically-generated chiral building blocks*", Tetrahedron: Asymmetry, vol. 9, pp. 1951-1965 (1998).

ISOQUINOLINE DERIVATIVES AS CALPAIN INHIBITORS

This application is a 371 of PCT/ES05/70171 filed Dec. 05, 2005.

FIELD OF THE ART

The present invention comes within the field of enzyme inhibitors with therapeutic activity, more specifically calpain inhibitors.

STATE OF THE ART

Calpain, or $Ca^{2+}$-activated neutral proteases (CANP, E.C. 3.4.22.17), are a family of cysteine proteases with a very active metabolic role. Although their natural substrate has not been clearly determined, these enzymes catalyse the hydrolysis of a variety of proteins involved in signal transduction, in cytoskeleton remodelling, in the regulation of the cell cycle and in apoptosis (*Adv. Pharmacol.* 1996, 37, 117). In mammals, the calpain family includes several tissue-specific isoforms and two ubiquitous isoenzymes: β-calpain (or calpain I) and m-calpain (or calpain II), which require micromolar and millimolar quantities respectively of $Ca^{2+}$ for their activation in vitro. Structural studies using X-ray diffraction have shown that each isoform consists of a large subunit (~80 kDa), which presents a cysteine protease domain of the papain type, and a small subunit (~30 kDa), which is common to each isoenzyme. The C-terminal ends of each subunit have domains able to bind $Ca^{2+}$ (calmoduline type domain) (*FEBS Lett.* 2001, 501, 111).

Overactivation of calpain, which can occur when the intracellular concentration of $Ca^{2+}$ increases, is involved in numerous diseases, such as cerebral and cardiac ischaemias, cerebral ictus, Alzheimer, Parkinson, Huntington, muscular distrophy, cataracts, demyelinating diseases (such as multiple sclerosis) and other degenerative diseases (*Pathophysiology* 1999, 6, 91; *Brain Res. Rev.* 2003, 42, 169).

The main application of selective inhibitors of calpain is as neuroprotector agents. In the therapeutic area related to neuroprotection, a range of strategies has been used so far. Agents have been used which act on the membrane depolarisation and the entry of $Ca^{2+}$ into cells, or which prevent the production of free radicals (antioxidants), or which are antagonists of the action of neurotransmitters (*J. Clinical Neurosci.* 2002, 9, 4). A great deal of attention has recently been paid to drugs capable of blocking the NMDA receptors for glutamate; nevertheless, the blocking of ionotropic receptors of excitatory amino acids cannot be an ideal method for preventing excitotoxic action since these drugs have psychotomimetic side effects (*Pharmacol. Ther.* 1999, 81, 163; *Neurobiol. Disease* 2003, 12, 82). An interesting alternative for achieving neuroprotection is the blocking of "post-receptor" cell phenomena which are physiologically silenced, in other words, the search for selective blockers of catabolic cascades induced by excitotoxic agents. These potential drugs with intracellular action could, when acting on metabolic routes which are activated during neurodegeneration, foreseeably permit a more efficient and selective neuroprotector action.

The overactivation of calpain requires a continual increase in the intracellular concentrations of $Ca^{2+}$, and this enzyme is latent in cells at rest [in other words, with "normal" $Ca^{2+}$ levels]. Therefore, the inhibition of calpain is presented as a suitable treatment in neurodegenerative diseases. On the basis of its characteristics, the inhibition of calpain would foreseeably have fewer side effects in human therapeutics than the blocking of metabolic processes prior to their activation in pathological processes, as is the case with antagonism of the NMDA receptor of glutamate and aspartate, due to the fact that calpain is not activated under "normal" physiological conditions and that the action of excitatory amino acids is essential for the normal functioning of the nervous system.

Moreover, powerful and selective inhibitors of calpain are very useful as work tools for studying the action mechanism of this protease, along with its role in certain physiological processes.

In addition, differentially substituted isoquinoline derivatives have been used as pharmacophores with a range of different biological activities (U.S. Pat. No. 5,576,435; Eur. J. Pharmacology. 2004, 501, 111). Also, amino acids and related compounds, such as amino carbonylic compounds, possess a range of different biological properties (*J. Med. Chem.* 2002, 45, 4762; *Bioorg. Med. Chem. Lett.* 2000, 10, 1497).

Reversible and irreversible inhibitors of calpain have been described (*Trends Mol. Medicine* 2001, 7, 355; U.S. Pat. No. 6,103,720; WO-9641638; U.S. Pat. No. 5,541,290; ES-200301125; ES-200401104; *Bioorg. Med. Chem. Lett* 2004, 14, 2753; *Chemistry & Biodiversity* 2004, 1, 442). The most frequent structural features of these inhibitors are that they are peptides or peptidomimetics with few amino acids (between 2 and 6), hydrophobic and with some electrophile functionality, among which can be mentioned α-keto phosphonates, α-keto phosphinates, α-ketophosphines oxides, α-keto esters, α-keto acids, α-keto amides, trifluoromethylketones, aldehydes, methylsulphonium salts, epoxides, etc. These compounds apparently act on the papain type domain of the calpain, which leads to a relatively low selectivity, due to which they are frequently also inhibitors of other cysteine proteases (for example, papain) and even serine proteases. Also, the fact that these compounds are peptide derivatives means that, in some cases, they possess certain undesired pharmacological properties, such as inefficient transport via cell membranes or degradation by peptidase. Due in part to these drawbacks, a calpain inhibitor having therapeutic utility has not yet been found.

Our group has recently prepared a variety of calpain inhibitors characterised by being isoquinoline derivatives (*Adv. Synth. Catal.* 2002, 344, 855). Nevertheless, for these isoquinoline derivatives to be active as calpain inhibitors the presence of a peptide chain is needed (illustrative examples are compounds 1 and 2, which we will generically refer to as peptide-heterocycle hybrids), and the biological activity is highly dependent on the length of the peptide fragment, as revealed by the $IC_{50}$ values of compounds 1 and 2. Nevertheless, our first results indicated that simple derivatives of isoquinoline, in which there is no peptide chain, are not calpain inhibitors, as illustrated for compound 3.

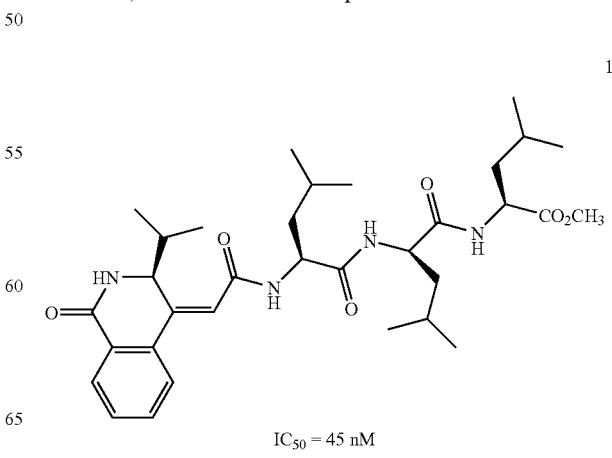

$IC_{50} = 45$ nM

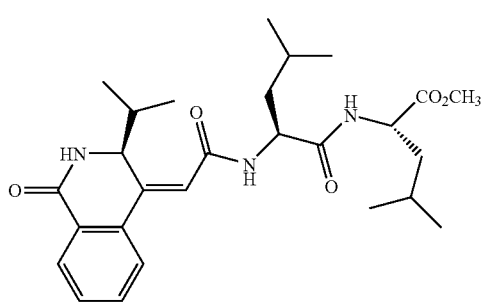

IC$_{50}$ = 100 μM

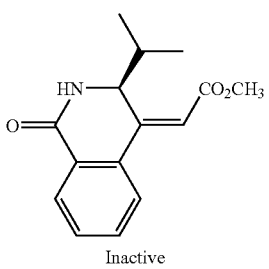

Inactive

The extension of the research into isoquinoline derivatives as calpain inhibitors has enabled us to discover that when the substituent in position 3- of the isoquinoline ring is a sec-butyl group, the inhibitory activity of calpain increases spectacularly, and the presence of peptide chains is not absolutely necessary for achieving such biological activity. The fact that the presence of peptide chains is not necessary in this type of compound notably increases its useful therapeutic potential as enzyme inhibitors: it can be expected that these isoquinoline derivatives without any peptide chain will be metabolically more stable and their cell transport will be more efficient than peptide-heterocycle hybrids.

BRIEF DESCRIPTION OF THE INVENTION

The present invention relates to compounds derived from partially-reduced isoquinoline with activity as calpain inhibitor. One inventive compound is an ester or amide derived from (3-sec-butyl-1-oxo-2,3-dihydro-1H-isoquinolin-4-yliden)-acetic acid and (3-sec-butyl-1-thioxo-2,3-dihydro-1H-isoquinolin-4-yliden)-acetic acid, including compounds whose substituent in position 4- of the isoquinoline fragment are structures related to amino acids, including fragments of aminocarbonylic compounds, which are bonded to the isoquinoline fragment by a carbonylmethylidene group.

DESCRIPTION

The present invention relates to a compound characterised in that it has a partially-reduced isoquinoline structure with substitution of a sec-butyl group in position 3, and of formula I or II,

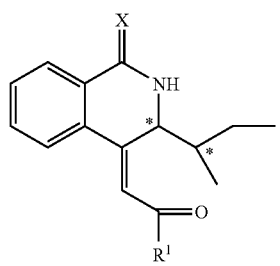

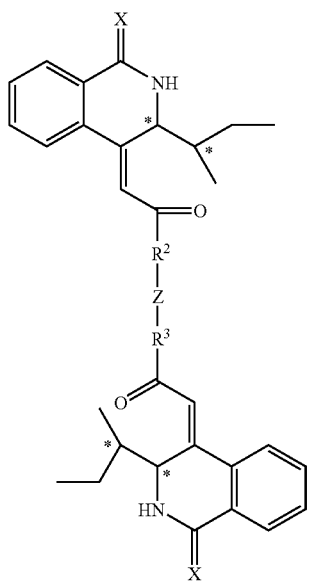

in which:
  the group X is oxygen (O) or sulphur (S), indifferently,
  the asterisk (*) represents a stereogenic centre, of configuration (R) or (S), indifferently,
  the group R$^1$ is independently selected from the group consisting of:
    NH$_2$,
    NHR$^4$ in which R$^4$ represents an alkyl group, aryl group, an amino acid derivative or a peptide derivative,
    NR$^5$R$^6$ in which R$^5$ and R$^6$ are independently selected from among an alkyl group, aryl group, an amino acid derivative, a peptide derivative, and groups R$^5$ and R$^6$ forming a cyclic system,
    OH,
    OR$^7$ in which R$^7$ represents an alkyl or aryl group;
  the groups R$^2$ and R$^3$ are the same or different and are independently selected from among the groups O (oxygen), NH or NR$^8$ in which R$^8$ represents an alkyl or aryl group
  Z is selected from among the groups,
    alkyl with between 2 and 8 carbon atoms,
    aryl,
    arylalkyl,
    oxyalkyl chain independently containing between 1 and 3 atoms of oxygen and between 2 and 10 atoms of carbon,
    fragment derived from amino acid or peptide.
The following are preferred compounds:
methyl (S,S,Z)-(3-sec-butyl-1-oxo-2,3-dihydro-1H-isoquinolin-4-yliden)-acetate (7),
(S,S,Z)-(3-sec-butyl-1-oxo-2,3-dihydro-1H-isoquinolin-4-yliden)-acetic acid (8), iso-propyl (S,S,Z)-(3-sec-butyl-1-oxo-2,3-dihydro-1H-isoquinolin-4-yliden)-acetate (9),
1-butyl (S,S,Z)-(3-sec-butyl-1-oxo-2,3-dihydro-1H-isoquinolin-4-yliden)-acetate (10),
benzyl (S,S,Z)-(3-sec-butyl-1-oxo-2,3-dihydro-1H-isoquinolin-4-yliden)-acetate (11),
(S,S,S,S,Z,Z,Z)-(3-sec-butyl-1-oxo-2,3-dihydro-1H-isoquinolin-4-yliden)-but-2-enyl 4-[2-3-sec-butyl-1-oxo-2,3-dihydro-1H-isoquinolin-4-yliden)-acetoxyl]-acetate (12),
(S,S,S,S,Z,Z)-(3-sec-butyl-1-oxo-2,3-dihydro-1H-isoquinolin-4-yliden)-but-2-inyl 4-[2-3-sec-butyl-1-oxo-2,3-dihydro-1H-isoquinolin-4-yliden)-acetoxyl]-acetate (13),
(S,S,S,S,Z,Z)-4-[2-(3-sec-butyl-1-oxo-2,3-dihydro-1H-isoquinolin-4-yliden)-acetoxyl]-benzyl (3-sec-butyl-1-oxo-2,3-dihydro-1H-isoquinolin-4-yliden)-acetate (14),
(S,S,Z)-N-benzyl-2-(3-sec-butyl-1-oxo-2,3-dihydro-1H-isoquinolin-4-yliden)-acetamide (15),
(S,S,Z)-N-(3-acetyl-phenyl)-2-(3-sec-butyl-1-oxo-2,3-dihydro-1H-isoquinolin-4-yliden)-acetamide (16),
(S,S,Z)-N-(2'-amino-biphenyl-2-yl)-2-(3-sec-butyl-1-oxo-2,3-dihydro-1H-isoquinolin-4-yliden)-acetamide (17),
(S,S,S,S,Z,Z)-2,2'-bis-[(3-sec-butyl-1-oxo-2,3-dihydro-1H-isoquinolin-4-yliden)-acetylamino]biphenyl (18),
(S,S,S,Z)-9H-fuorene-9-ylmethyl (1-{2'-[2-(3-sec-butyl-1-oxo-2,3-dihydro-1H-isoquinolin-4-yliden)-acetylamino]-biphenyl-2-ylcarbamoyl}-2-methyl-propyl)-carbamate (19),
(S,S,S,Z)-9H-fuorene-9-ylmethyl (1-{2'-[2-(3-sec-butyl-1-oxo-2,3-dihydro-1H-isoquinolin-4-yliden)-acetylamino]-biphenyl-2-ylcarbamoyl}-2-phenyl-ethyl)-carbamate (20),
(S,S,S,S,Z)-9H-fuorene-9-ylmethyl (1-{2'-[2-(3-sec-butyl-1-oxo-2,3-dihydro-1H-isoquinolin-4-yliden)-acetylamino]-biphenyl-2-ylcarbamoyl}-2-methyl-butyl)-carbamate (21),
(S,S,S,Z)-2-amino-N-{2'-[2-(3-sec-butyl-1-oxo-2,3-dihydro-1H-isoquinolin-4-yliden)-acetylamino]-biphenyl-2-yl}-3-methyl-butyramide (22),
(S,S,S,Z)-2-amino-N-{2'-[2-(3-sec-butyl-1-oxo-2,3-dihydro-1H-isoquinolin-4-yliden)-acetylamino]-biphenyl-2-yl}-3-phenyl-propionamide (23),
(S,S,S,S,Z)-2-amino-N-{2'-[2-(3-sec-butyl-1-oxo-2,3-dihydro-1H-isoquinolin-4-yliden)-acetylamino]-biphenyl-2-yl}-3-methyl-pentanamide (24),
methyl (S,S,S,S,S,S,Z)-2-{2-[2-(3-sec-butyl-1-oxo-2,3-dihydro-1H-isoquinolin-4-yliden)-acetylamino]-3-methyl-pentanoylamino}-3-methyl-pentanoate (25),
methyl (S,S,S,S,S,S,S,S,Z)-2-(2-{2-[2-(3-sec-butyl-1-oxo-2,3-dihydro-1H-isoquinolin-4-yliden)-acetylamino]-3-methyl-pentanoylamino}-3-methyl-pentanoylamino)-3-methyl-pentanoate (26),
methyl (S,S,S,S,Z)-2-{2-[2-(3-sec-butyl-1-oxo-2,3-dihydro-1H-isoquinolin-4-yliden)-acetylamino]-3-methyl-butirylamino}-3-phenyl-propionate (27),
methyl (S,S,Z)-(3-sec-butyl-1-thioxo-2,3-dihydro-1H-isoquinolin-4-yliden)-acetate (28),
(S,S,Z)-(3-sec-butyl-1-thioxo-2,3-dihydro-1H-isoquinolin-4-yliden)-acetic acid (29),
and
methyl (S,S,S,S,S,S,Z)-2-{2-[2-(3-sec-butyl-1-thioxo-2,3-dihydro-1H-isoquinolin-4-yliden)-acetylamino]-3-methyl-pentanoylamino}-3-methyl-pentanoate (30),
and any of their isomers.

The following synthetic intermediates are also especially preferred compounds of the present invention:
methyl (S,S)-3-methyl-2-(2-iodobenzoylamino)-pentanoate (4),
(S,S)—N-[(1-hydroxymethyl-2-methyl)-butyl]-2-iodo-benzamide (5),
and
methyl (S,S,E)-5-methyl-4-(2-iodobenzoylamino)-2-heptenoate (6), and any of their isomers.

The synthesis of compounds of general formula I and II of the present invention has been carried out using standard methods in organic synthesis, which are known to experts in the art (*Chemical Approaches to the Synthesis of Peptides and Proteins*, CRC Press, Boca Raton, 1997; *Comprehensive Organic Synthesis*. Pergamon Press, 1991; Synlett 2000, 509; *Adv. Synth. Catal.* 2001, 343, 360; *Topics Current Chemistry* 1999, 204, 127; *Bull. Soc. Chim. Belg.* 1978, 87, 229). As an illustrative example, though without being limiting, the compounds described in this patent have been prepared starting from the corresponding isomer of (3-sec-butyl-1-oxo-2,3-dihydro-1H-isoquinolin-4-yliden)-acetic acid (III) or from the corresponding isomer of (3-sec-butyl-1-thioxo-2,3-dihydro-1H-isoquinolin-4-yliden)-acetic acid (IV). The synthesis of compounds III and IV is indicated below using the following compounds as intermediates, which are also the object of this invention,
any isomer of methyl (3-sec-butyl-1-oxo-2,3-dihydro-1H-isoquinolin-4-yliden)-acetate (A),
any isomer of methyl 5-methyl-4-(2-iodobenzoylamino)-2-heptenoate (B),
any isomer of N-[(1-hydroxymethyl-2-methyl)-butyl]-2-iodo-benzamide (C),
and
any isomer of methyl 2-(2-iodobenzoylamino)-3-methyl-pentanoate (D).

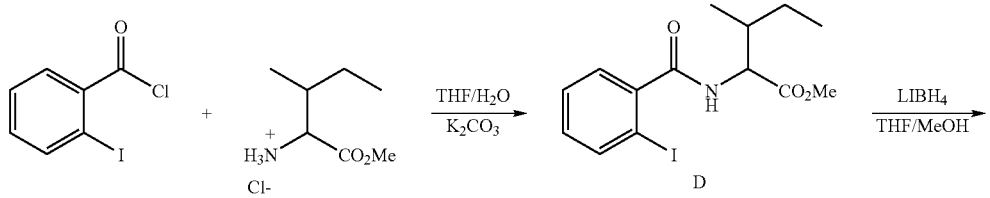

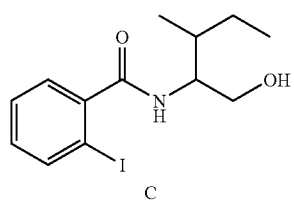
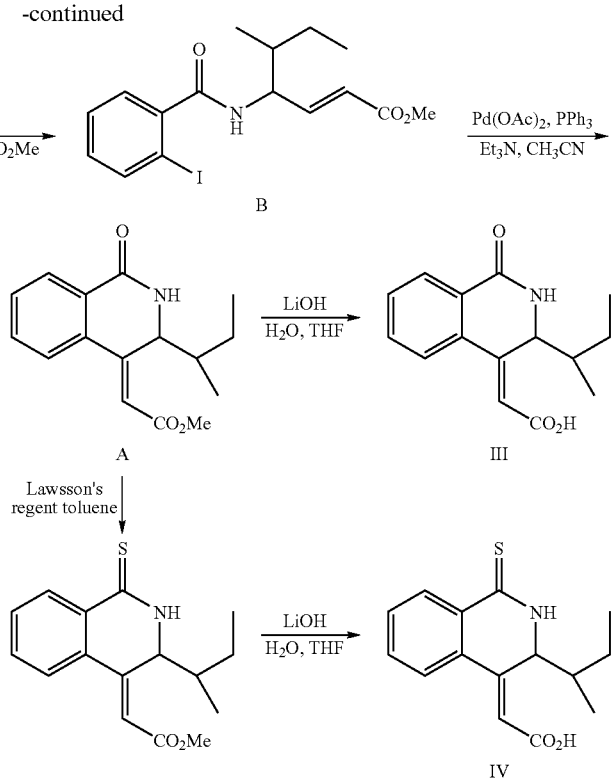

Due to the fact that the main functionality present in compounds I and II (as indicated by the substituents $R^1$, $R^2$ and $R^3$) is the amide or ester, the essential reaction in the preparation of compounds of type I and II is an acylation reaction between an acid or an acid derivative, as electrophile, and an amine or alcohol, as nucleophile. The synthetic strategy of compounds of formula I and II depends on the structure of the groups $R^1$, $R^2$ and $R^3$, and also on whether these groups are the same or different. A special type of compound of type I and II, forming the object of this invention, are those of type V in which there exist chains of amino acids, peptides and related compounds, joined to the isoquinoline fragment via an acetylmethylidene group. These compounds are prepared by transformations that are habitual in organic synthesis and which are known to experts in the art, using suitable derivatives of amino acids, peptides and related compounds.

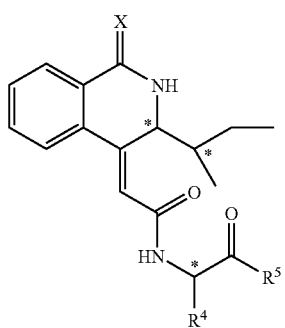

V

Alcohols, amines, amino acids, peptides and derivatives thereof used in the synthesis of compounds of formula I and II are commercial or prepared by standard methods in organic synthesis. In some cases, especially with non-natural amino acids of the series D-, and related compounds, biocatalytic methods using the enzyme acylase as biocatalyst have been applied (*Tetrahedron: Asymmetry* 1998, 9, 1951-1965).

When peptides have been used as nucleophiles or electrophiles in the synthesis of compounds I and II, their synthesis has been carried out by standard methods in amino acid and peptide chemistry. The groups terc-butoxycarbonyl (Boc), benzyloxycarbonyl (Cbz) and fluorenylmethoxycarbonyl (Fmoc) have been used as protection for the amino groups; the carboxy groups have been protected as aliphatic esters (methyl, ethyl or benzyl). The coupling reaction for the synthesis of these peptides used as nucleophiles has been done using standard methodologies: by activation of the carbonyl group as acid chloride, or via the formation of active esters (for example, pentafluorophenyl), or via the mixed anhydride, or by "in situ" activation of the carbonyl group (by treatment of the acid with a combination of carbodiimide and 1-hydroxybenzotriazol or related methods) (*Chemical Approaches to the Synthesis of Peptides and Proteins*, CRC Press, Boca Raton, 1997).

An essential characteristic of the compounds of the present invention is that they are calpain inhibitors. There exist various isoforms of calpain, which are structurally very similar to each other and, as far as is known, share the same mechanism of action. The two most abundant are micro-calpain (or calpain I) and milli-calpain (or calpain II), which are differentiated in in vitro tests in the concentration of $Ca^{2+}$ necessary for their activation. As the two isoforms of the enzyme are very similar to each other, it has been found in many examples in the literature that the calpain inhibitors are inhibitors of both isoenzymes (*Adv. Synth. Catal.* 2002, 344, 855). So, in the present invention, when we mention calpain, we are refer-ring to the two isoforms (or isoenzymes) which are included in the definition of calpain. Therefore, another object of the present invention is the use of a compound of formula I or II as calpain inhibitor.

The capacity to inhibit calpain has been quantified in terms of the value of $IC_{50}$, which is defined as the concentration of inhibitor that reduces the catalytic activity of an enzyme by half. The lower the value of $IC_{50}$, the more powerful the inhibitor. Inhibition results on calpain I (the most relevant from a physiological point of view) of some compounds of the present invention are shown in table 1 and in FIG. 1. Given that calpain II, also known as milli-calpain, needs a greater amount of $Ca^{2+}$ for activation, it might not possibly have such a relevant physiological role since such a concentration of $Ca^{2+}$ would cause cell death before the milli-calpain could become activated. For this reason, the inhibition tests have been performed for calpain I, though they can be extrapolated for calpain II.

TABLE 1

Representative results on the inhibition of calpain by compounds forming the object of this invention.

| Compounds | $IC_{50}$ |
| --- | --- |
| 7 | 25 nM |
| 11 | 124 μM |
| 12 | 85 μM |
| 13 | 59 μM |
| 14 | 5 μM |
| 15 | 140 μM |
| 16 | 130 μM |
| 17 | 86 nM |
| 18 | 742 nM |
| 19 | 100 μM |
| 20 | 48 μM |
| 21 | 5 μM |
| 22 | 17 μM |
| 23 | 7 μM |
| 24 | 50 μM |
| 25 | 447 nM |
| 26 | 159 nM |
| 27 | 626 nM |
| 28 | 38 μM |

Some of the compounds represented in FIG. 1 are very potent inhibitors of calpain and they can be useful in the design of compounds having therapeutic applications. Owing to the fact that it has been found that overactivation of calpain is involved in numerous degenerative diseases, an additional object of the present invention is the use of a compound of formula I or II for the treatment or prevention of degenerative diseases and for preparing a drug for the preventive or therapeutic treatment of a degenerative disease, and especially when the degenerative disease is selected from among cerebral ischaemic, cardiac ischaemia, cerebral ictus, Alzheimer, Parkinson, Huntington, muscular distrophy, cataracts and demyelinating diseases, and especially if the demyelinating disease is multiple sclerosis (*Pathophysiology* 1999, 6, 91; *Brain Res. Rev.* 2003, 42, 169).

EXAMPLES

Figure 1:
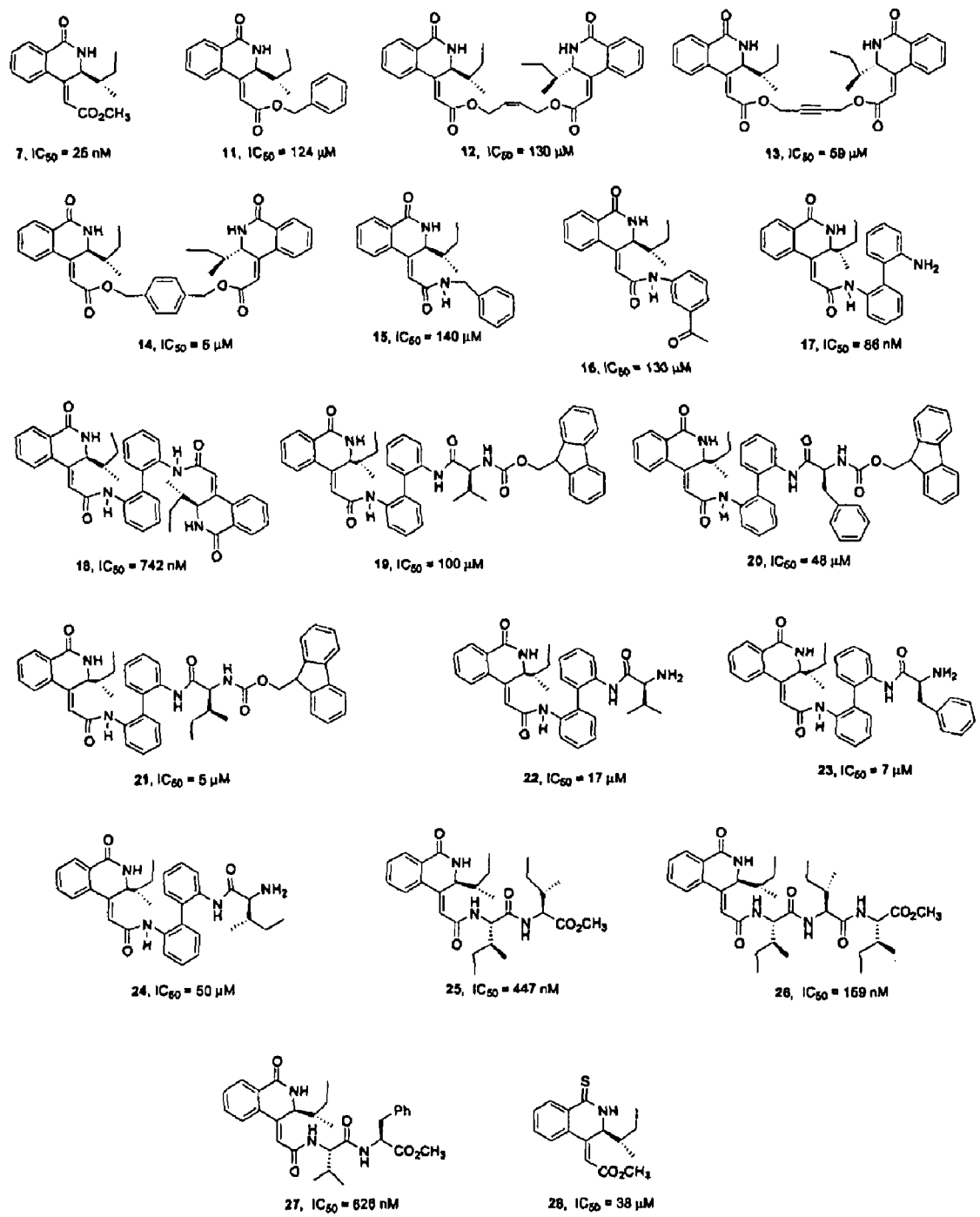
FIG. 1 shows results of the study on derivatives of (3-sec-butyl-1-oxo-2,3-dihydro-1H-isoquinolin-4-yliden)-acetic acid and on derivatives of (3-sec-butyl-1-thioxo-2,3-dihydro-1H-isoquinolin-4-yliden)-acetic acid, forming the objects of the present invention, and their biological activity as inhibitors of calpain I.

As illustrative examples, though without being limiting, the experimental procedures and spectroscopic and analytical data of some isoquinoline derivatives of formulas I or II are given, along with tests on their biological activity are included.

Example 1

Synthesis of methyl (S,S)-3-methyl-2-(2-iodobenzoylamino)-pentanoate (4)

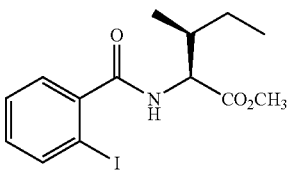

4

To a solution of L-isoleucine methyl ester hydrochloride (13.07 g, 72.0 mmol) in THF (300 mL) and $H_2O$ (300 mL), $K_2CO_3$ was added (39.80 g, 288 mmol). The mixture was cooled to 0° C. and after stirring for 5 minutes, 2-iodobenzoyl chloride (19.18 g, 72.0 mmol) was added. The mixture was stirred at 0° C. for 30 minutes and was then left to slowly reach room temperature overnight. THF was eliminated and the aqueous phase was extracted with EtOAc (3×50 mL). The organic phases were washed with brine and dried over $MgSO_4$. Once the solvent had been eliminated in vacuo the raw product was obtained, which was purified by recrystallisation from EtOAc/hexane to give 4 (16.7 6; 62%). White solid.

m.p.: 67-70° C.

$[\alpha]_D$=+9.2 (c=1.0, $CHCl_3$).

IR (KBr) v: 3436, 3294, 2964, 1743, 1644, 1585, 1525, 1463, 1201, 1015 $cm^{-1}$.

$^1$H-NMR (300 MHz, $CDCl_3$) δ: 7.87 (m, 1H, H—C (3')); 7.41 (m, 2H, H—C (5')), H—C (6'); 7.11 (m, 1H, H—C (4')); 6.33 (broad d, J=8.1, 1H, NH); 4.83 (dd, J=8.1, 4.6, 1H, H—C (2)); 3.78 (s, H, $CO_2Me$), 2.06 (m, 1H, H—C (3)); 1.52 (m, 1H, $H_a$—C (4)); 1.29 (m, 1H, $H_b$—C (4)); 1.03 (d, J=6.8, 3H, Me-C(3)); 0.97 (t, J=7.6, 3H, H—C(5)) ppm.

$^{13}$C-NMR (50 MHz, $CDCl_3$) δ: 171.9 ($CO_2Me$); 168.7 (CONH); 141.7 (C(1')); 139.9 (C(3')); 131.2 (C(4')); 128.3, 128.0 (C(5')), (C(6')); 92.2 (C(2')); 56.7 (C(2)); 52.1 ($CO_2Me$); 38.0 (C(3)); 25.2 (C(4)); 15.6 (Me-C(3)); 11.6 (C(5)) ppm.

MS ($ESu^+$) m/e: 376 ($[M+H]^+$), 398 ($[M+Na]^+$), 773 ($[2M+H]^+$).

EA: Calculated for $C_{14}H_{18}INO_3$: C, 44.82; H, 4.84; N, 3.73.

Found: C, 45.12; H, 5.10; N, 4.00.

Example 2

Synthesis of (S,S)—N-[(1-hydroxymethyl-2-methyl)-butyl]-2-iodo-benzamide (5)

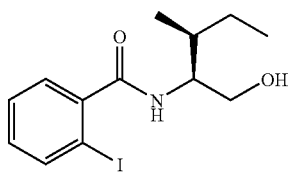

5

To a solution of 4 (8.44 g, 22.5 mmol) in THF (50 mL) at −10° C., LiBH$_4$ was added (1.47 g, 67.5 mmol). Immediately afterwards MeOH (45 mL) was slowly added, the mixture was stirred at −10° C. for 10 minutes and then left to reach room temperature. After that, H$_2$O was added, THF was eliminated in vacuo and the aqueous phase was extracted with EtOAc (3×50 mL). The organic phases were washed with brine and dried over MgSO$_4$. Once the solvent had been eliminated in vacuo the raw product was obtained, which was purified by column chromatography using hexane/EtOAc as eluent (1:1 to 1.9) and then EtOAc, obtaining 5 (6.6 g, 85% yield). White solid.

m.p.: 125-126° C.
[α]$_D$=−27.8 (c=1.0, CHCl$_3$).
IR (KBr) v: 3410, 3295, 1628, 1544, 1076, cm$^{-1}$.
$^1$H-NMR (400 MHz, CDCl$_3$, mixture of conformers M and m, 4:1) δ: 7.81 (m, 0.7H, H—C (3'), M); 7.72 (m, 0.3H, H—C (3'), m); 7.50-7.31 (m, 2H, H—C (5') H—C (6'), M+m); 7.10-7.04 (m, 1H, H—C (4'), M+m); 6.42 (d, J=8.1, 0.2H, NH, m); 6.06 (broad d, J=8.1, 0.8H, NH, M); 3.99-3.85 (m, 1H, H—C (2), M+m); 3.85-3.72 (m, 2H, H—C (1), M+m); 2.88 (broad t, J=5.4, 0.2H, OH, m); 2.62 (broad t, J=5.4, 0.8H, OH, M); 1.80-1.50 (m, 2H, H—C (4), M+m); 1.28-1.14 (m, 1H, H—C (3), M+m); 0.97 (d, J=6.8, 3H, Me-C(3)); 0.92 (t, J=7.5, 3H, H—C(5)) ppm.
$^{13}$C-NMR (50 MHz, CDCl$_3$) δ: 170.0 (CONH); 142.7 (C(1')); 139.7 (C(3')); 131.1 (C(4')); 128.5, 128.1 (C(5'), (C(6')); 92.3 (C(2')); 36.2 (C(1)); 56.4 (C(2)); 35.5 (C(3)); 25.6 (C(4)); 15.6 (Me-C(3)); 11.3 (C(5)) ppm.
MS (ES$^+$) m/e: 348 ([M+H]$^+$), 370 ([M+Na]$^+$), 717 ([2M+Na]$^+$).
EA: Calculated for C$_{13}$H$_{18}$INO$_2$: C, 44.97; H, 5.23; N, 4.03.
Found: C 45.11, H 5.26, N 4.18.

Example 3

Synthesis of methyl (S,S,E)-5-methyl 4-(2-iodobenzoylamino)-2-heptenoate (6)

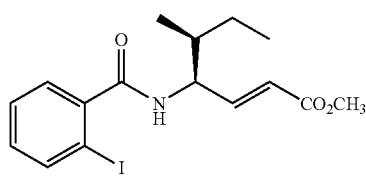

6

To a commercial solution of 2M oxalyl chloride in anhydrous CH$_2$Cl$_2$ (10.33 mL, 20.8 mmol) diluted with the same solvent (12 mL) at −78° C. was added dropwise a solution of anhydrous DMSO (2.9 mL, 41.0 mmol) in anhydrous CH$_2$Cl$_2$ (30 mL). The mixture was stirred for 30 minutes at −78° C. after which a solution of the alcohol 5 was added (4.44 g, 12.8 mmol) in anhydrous CH$_2$Cl$_2$ (25 mL) dropwise by means of a cannula. The mixture was stirred for 1 hour at −78° C. and Et$_3$N was then added (10.26 ml, 74.0 mmol) dropwise. After stirring for approximately 1 hour at −78° C., when the oxidation of the aldehyde was complete (tic), Ph$_3$P=CHCO$_2$Me was added (6.0 g, 19.0 mmol) and the reaction was then left to slowly reach room temperature overnight. Finally, the solvent was eliminated in vacuo obtaining a raw product, which was purified by column chromatography using hexane/EtOAc as eluent (4:1 to 1.1) providing the E isomer of the unsaturated N-benzoylamino ester 6 (4.1 g, 80% yield). White solid.

m.p.: 124-125° C.
[α]$_D$=+1.7 (c=1.0, CHCl$_3$).
IR (KBr) v: 3347, 3275, 2958, 1721, 1640, 1531 cm$^{-1}$.
$^1$H-NMR (300 MHz, CDCl$_3$) δ: 7.85 (d, J=7.8, 1H, H—C (3')); 7.37 (m, 2H, H—C (5'), H—C (6')); 7.10 (m, 1H, H—C (4')); 6.92 (dd, J=15.8, 5.9, 1H, H—C(3)); 6.05 (dd, J=15.8, 1.7, 1H, H—C (2)); 5.93 (broad d, J=8.8, 1H, NH); 4.79 (m, 1H, H—C (4)); 3.72 (s, 3H, CO$_2$Me); 1.79 (m, 1H, H—C(5)); 1.54 (m, 1H, H$_a$—C (6)); 1.22 (m, 1H, H$_b$—C (6)); 0.97 (m, 6H, Me-C(5), H—C(7)) ppm.
$^{13}$C-NMR (50 MHz, CDCl$_3$) δ: 168.7 (CONH); 166.5 (CO$_2$Me); 145.9 (C(3)); 142.0 (C(1')); 139.9 (C(3')); 131.2 (C(4')); 128.3, 128.2 (C(5'), C(6')); 122.0 (C(2)); 92.1 (C(2')); 54.8 (C(4)); 51.7 (CO$_2$Me); 38.7 (C(5)); 25.4 (C(6)); 15.4 (Me-C(5)); 11.6 (C(7)) ppm.
MS (ES$^+$) m/e: 402 ([M+H]$^+$), 424 ([M+Na]$^+$), 803 ([2M+H]$^+$), 825 ([2M+Na]$^+$).
EA: Calculated for C$_{16}$H$_{20}$INO$_3$: C 47.89; H, 5.02; N, 3.49.
Found: C 48.11, H 5.13, N 3.61.

Example 4

Synthesis of methyl (S,S,Z)-(3-sec-butyl-1-oxo-2,3-dihydro-1H-isoquinolin-4-yliden)-acetate (7)

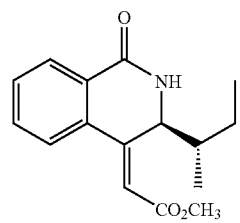

7

A mixture of the ester 6 (4.17 g, 10.4 mmol), Pd(OAc)$_2$ (80 mg, 0.035 mmol), Ph$_3$P (288 mg, 1.08 mmol) and Et$_3$N (3.2 mg, 20.6 mmol) in anhydrous CH$_3$CN (250 mL) was refluxed for 3 days under argon with vigorous stirring. The mixture was then left to reach room temperature following by the addition of H$_2$O (250 mL), and it was extracted with CHCl$_3$ (3×50 mL). The organic phases were washed with brine and dried over MgSO$_4$. Once the solvent had been eliminated in vacuo the raw product was obtained, which was purified by column chromatography using hexane/EtOAc as eluent (4:1 to 2:3) to give the compound 7 (2.4 g, 85% yield). White amorphous solid.

[α]$_D$=−365.8 (c=0.5, CHCl$_3$).
IR (KBr) v: 3434, 1715, 1669, 1568, 1195, 1167, 774 cm$^{-1}$.

¹H-NMR (500 MHz, CDCl₃) δ: 8.13 (m, 1H, H—C (8')); 7.57 (m, 3H, H—C (5'), H—C (6'), H—C (7')); 6.60 (broad d, J=3.4, 1H, NH); 6.34 (s, 1H, H—C(2)); 5.45 (m, 1H, H—C (3')); 3.77 (s, 3H, CO₂Me); 1.61 (m, 1H, H—C(1")); 1.45 (m, 1H, H$_a$—C (2")); 1.15 (m, 1H, H$_b$—C (2")); 0.87 (d, J=6.8, 3H, Me-C(1")); 0.81 (t, J=7.6, 3H, H—C(3")) ppm.

¹³C-NMR (50 MHz, CDCl₃) δ: 165.4 (CONH); 164.0 (CO₂Me); 150.7 (C(4')); 135.3 (C(4a')); 132.7, 130.5 (C(5) or C(6') or C(7')); 128.4 (C(8a'); 127.9 (C(8')); 123.8 (C(5') or (C(6') or C(7')); 116.4 (C(2)); 55.8 (C(3')); 51.5 (CO₂Me); 41.5 (C(1")); 24.4 (C(2")); 15.1 (Me-C(1')); 11.0 (C(3")) ppm.

MS (ES⁺) m/e: 274 ([M+H]⁺), 296 ([M+Na]⁺), 547 ([2M+H]⁺), 569 ([2M+Na]⁺).

EA: Calculated for $C_{16}H_{19}NO_3$: C 70.31; H, 7.01; N, 5.12. Found: C, 70.15; H, 7.02; N, 5.04.

Example 5

Synthesis of (S,S,Z)-(3-sec-butyl-1-oxo-2,3-dihydro-1H-isoquinolin-4-yliden)-acetic acid (8)

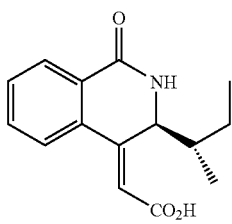

8

To a solution of 7 (273 mg, 1.0 mmol) in a 1:1 mixture of THF—H₂O (10 mL) at room temperature was added a solution of LiOH (83.9 mg, 2.0, mmol) in H₂O (2 mL). The mixture was stirred at room temperature overnight, and was then acidified with 5% HCl to pH=2. THF was eliminated in vacuo and the aqueous phase was extracted with EtOAc (3×50 mL). The organic phases were washed with brine and dried over MgSO₄. Once the solvent had been eliminated in vacuo the raw product was obtained, which was purified by recrystallisation of EtOAc/hexane to give the acid 8 (140 mg, 54% yield) as a white solid.

m.p.: 215-216° C. (with prior softening)

$[\alpha]_D$=−333.8 (c=0.49, DMF).

IR (KBr) ν: 3435, 2966, 1674, 1306 cm⁻¹.

¹H-NMR (300 MHz, DMSO-d₆) δ: 12.46 (broad s, 1H, CO₂H); 8.60 (d, J=4.9, 1H, NH); 7.91 (dd, J=7.3, 1.5, 1H, H—C(8')); 7.75 (dd, J=7.9, 1.3, 1H, H—C(5')); 7.64-7.53 (m, 2H, H—C(6'), H—C(7')); 6.36 (s, 1H, H—C(2)); 5.24 (dd, J=7.7, 4.9, 1H, H—C(3')); 1.47 (m, 1H, H$_a$—C (2")); 1.45 (m, 1H, H—C (1")); 1.16 (m, 1H, H$_b$—C (2")); 0.74 (m, 6H, Me-C(1"), H—C(3")) ppm.

¹³C-NMR (50 MHz, DMSO-d₆) δ: 166.7 (CONH); 162.5 (CO₂H); 149.1 (C(4')); 135.1 (C(4a')); 132.6, 130.3 (C(6'), C(7')); 128.7 (C(8a'); 127.0 (C(8')); 124.4 (C(5')); 117.6 (C(2)); 53.9 (C(3')); 41.2 (C(1")); 24.3 (C(2")); 15.0, 10.9 (Me-C(1'), C(3")) ppm.

MS (ES⁺) m/e: 260 ([M+H]⁺), 282 ([M+Na]⁺), 519 ([2M+H]⁺), 541 ([2M+Na]⁺).

EA: Calculated for $C_{16}H_{17}NO_3$: C 69.48; H, 6.61; N, 5.40. Found: C, 69.25; H, 7.00; N, 5.41.

Example 6

Reaction of the Acid 8 with Alcohols and Diols (General Procedure I)

Synthesis of Esters of the Acid 8

To a suspension of the acid 8 (100 mg, 0.38 mmol) in anhydrous CH₂Cl₂ (2.5 mL) at 0° C., SOCl₂ was added (0.28 mL, 3.8 mmol) dropwise. The mixture was stirred until reaching room temperature and then heated at reflux for approximately 1 h. The solvent was then eliminated at reduced pressure obtaining an oil which was dissolved in anhydrous CH₂Cl₂ (2.5 mL), to which was added the corresponding alcohol (0.76 mmol for monoalcohols and 0.15 mmol for diols) under argon, dissolved in anhydrous CH₂Cl₂ (2.5 mL). The reaction was then diluted with CH₂Cl₂ (50 mL) and extracted with a saturated aqueous solution of NaHCO₃ (3×50 mL). The organic phase was washed with brine and dried over MgSO₄. Once the solvent had been eliminated in vacuo the raw product was obtained, which was purified by column chromatography using hexane/EtOAc as eluent (4:1 to 1:1). The yields stated below refer to the overall process consisting of two reactions (formation of the acid chloride and synthesis of the esters).

Example 7

Synthesis of iso-propyl (S,S,Z)-(3-sec-butyl-1-oxo-2,3-dihydro-1H-isoquinolin-4-yliden)-acetate (9)

Following General Procedure I, compound 9 was obtained as a colourless oil (81 mg, 71% yield).

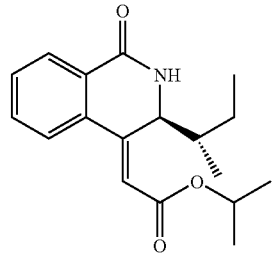

9

$[\alpha]_D$=−341.8 (c=0.25, CHCl₃).

IR (KBr) ν: 3429, 2968, 2876, 1708, 1672, 1372, 1181, 1107, 775 cm⁻¹.

¹H-NMR (400 MHz, CDCl₃) δ: 8.09 (m, 1H, H—C (8')); 7.55 (m, 3H, H—C (5'), H—C (6'), H—C (7')); 6.97 (broad s, 1H, NH); 6.28 (s, 1H, H—C(2)); 5.44 (dd, J=4.5, 2.4, 1H, H—C (3')); 5.07 (sep, J=6.2 1H, CHMe₂); 1.58 (m, 1H, H—C(1")); 1.43 (m, 1H, H$_a$—C (2")); 1.28 (d, J=6.2, 3H, CO₂CHMe₂); 1.26 (d, J=6.2, 3H, CO₂CHMe₂); 1.15 (m, 1H, H$_b$—C (2")); 0.86 (d, J=6.8, 3H, Me-C(1")); 0.78 (t, J=7.4, 3H, H—C(3")) ppm.

¹³C-NMR (50 MHz, CDCl₃) δ: 165.0 (CONH); 164.0 (CO₂CHMe₂); 149.8 (C(4')); 135.5 (C(4a')); 132.6, 130.4 (C(5') or C(6') or C(7')); 128.4 (C(8a'); 127.9 (C(8')); 123.8 (C(5') or (C(6') or C(7')); 117.5 (C(2)); 67.8 (CO₂CHMe₂); 55.8 (C(3')); 41.5 (C(1")); 24.4 (C(2")); 21.9 (CO₂CHMe₂); 15.1 (Me-C(1')); 11.0 (C(3")) ppm.

MS (ES⁺) m/e: 302 ([M+H]⁺), 324 ([M+Na]⁺), 603 ([2M+H]⁺), 625 ([2M+Na]⁺).

Example 8

Synthesis of 1-butyl (S,S,Z)-(3-sec-butyl-1-oxo-2,3-dihydro-1H-isoquinolin-4-yliden)-acetate (10)

Following General Procedure I, compound 10 was obtained as a white solid (82 mg, 69% yield).

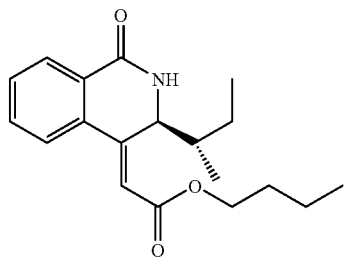

m.p.: 110-112° C.
[α]$_D$=−316.6 (c=0.5, CHCl$_3$).
IR (KBr) ν: 3467, 3311, 2927, 1707, 1667, 1599, 1186, 770 cm$^{-1}$.
$^1$H-NMR (300 MHz, CDCl$_3$) δ: 8.14 (m, 1H, H—C (8')); 7.59 (m, 3H, H—C (5'), H—C (6'), H—C (7')); 6.48 (broad s, 1H, NH); 6.35 (s, 1H, H—C(2)); 5.46 (dd, J=6.8, 3.4, 1H, H—C (3')); 4.18 (t, J=6.7, 2H, CO$_2$CH$_2$CH$_2$CH$_2$CH$_3$); 1.73-1.59 (m, 3H, H—C(1") CO$_2$CH$_2$CH$_2$CH$_2$CH$_3$); 1.50-1.42 (m, 3H, H$_a$—C (2"), CO$_2$CH$_2$CH$_2$CH$_2$CH$_3$); 1.18 (m, 1H, H$_b$—C (2")); 0.96 (t, J=7.4, CO$_2$CH$_2$CH$_2$CH$_2$CH$_3$); 0.88 (d, J=6.8, 3H, Me-C(1")); 0.82 (t, J=7.2, H, H—C(3")) ppm.
$^{13}$C-NMR (50 MHz, CDCl$_3$) δ: 165.6 (CONH); 164.7 (CO$_2$CH$_2$CH$_2$CH$_2$CH$_3$); 150.2 (C(4')); 135.5 (C(4a')); 132.8, 130.5 (C(5') or C(6') or C(7')); 128.1 (C(8a'); 126.9 (C(8')); 123.9 (C(5') or (C(6') or C(7')); 117.0 (C(2)); 64.4 (CO$_2$CH$_2$CH$_2$CH$_2$CH$_3$); 55.9 (C(3')); 41.5 (C(1")); 39.6 (CO$_2$CH$_2$CH$_2$CH$_2$CH$_3$); 24.4 (C(2")); 19.2 (CO$_2$CH$_2$CH$_2$CH$_2$CH$_3$); 15.1 (Me-C(1")); 13.7 (CO$_2$CH$_2$CH$_2$CH$_2$CH$_3$); 11.0 (C(3")) ppm.
MS (ES$^+$) m/e: 316 ([M+H]$^+$), 338 ([M+Na]$^+$), 631 ([2M+H]$^+$), 653 ([2M+Na]$^+$).

Example 9

Synthesis of benzyl (S,S,Z)-(3-sec-butyl-1-oxo-2,3-dihydro-1H-isoquinolin-4-yliden)-acetate (11)

Following General Procedure I, compound II was obtained as a white solid (69 mg, 50% yield).

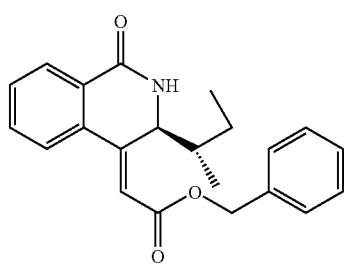

m.p.: 53-54° C.
[α]$_D$=−178.5 (c=0.005, CHCl$_3$).
IR (KBr) ν: 3435, 2927, 1710, 1669, 1159, 1028, 767, 695 cm$^{-1}$.
$^1$H-NMR (300 MHz, CDCl$_3$) δ: 8.14 (m, 1H, H—C (8')); 7.56 (m, 3H, H—C (5'), H—C (6'), H—C (7')); 7.39 (m, 5H, CO$_2$CH$_2$Ph); 6.86 (broad d, J=4.3, 1H, NH); 6.40 (s, 1H, H—C(2)); 5.46 (dd, J=7.1, 4.3, 1H, H—C (3')); 5.22 (s, 2H, CO$_2$CH$_2$Ph); 1.61 (m, 1H, H—C(1")); 1.44 (m, 1H, H$_a$—C (2")); 1.14 (m, 1H, H$_b$—C (2")); 0.87 (d, J=6.8, 3H, Me-C (1")); 0.81 (t, J=7.3, 3H, H—C(3")) ppm.
$^{13}$C-NMR (50 MHz, CDCl$_3$) δ: 165.2 (CONH); 163.8 (CO$_2$CHPh); 150.9 (C(4')); 135.6 C(4a')); 135.4 (C(Ph)); 132.7, 130.6 (C(5') or C(6') or C(7')); 128.6, 128.5, 128.4, 128.3, 128.1 (7 C, C(8') C(8a'), (C(Ph))); 123.9 (C(5') or (C(6') or C(7')); 116.5 (C(2)); 66.3 (CO$_2$CHPh); 55.9 (C(3')); 41.5 (C(1")); 24.4 (C(2")); 15.1 (Me-C(1")); 11.1 (C(3")) ppm.
MS (ES$^+$) m/e: 350 ([M+H]$^+$), 372 ([M+Na]$^+$), 699 ([2M+H]$^+$), 721 ([2M+Na]$^+$).

Example 10

Synthesis of (S,S,S,S,Z,Z,Z)-(3-sec-butyl-1-oxo-2,3-dihydro-1H-isoquinolin-4-yliden)-but-2-enyl 4-[2-3-sec-butyl-1-oxo-2,3-dihydro-1H-isoquinolin-4-yliden)-acetoxyl]-acetate (12)

Following General Procedure I, compound 12 was obtained as a white solid (35 mg, 41% yield).

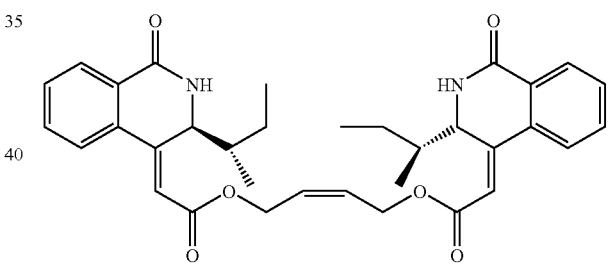

m.p.: 79-81° C.
[α]$_D$=−404.2 (c=0.12, CHCl$_3$).
IR (KBr) ν: 3429, 2964, 2927, 1714, 1671, 1273, 1157, 773 cm$^{-1}$.
$^1$H-NMR (300 MHz, CDCl$_3$) δ: 8.14 (m, 2H, H—C (8')); 7.56 (m, 6H, H—C (5'), H—C (6'), H—C (7')); 6.67 (broad d, J=4.6, 2H, NH); 6.34 (s, 2H, H—C(2)); 5.84 (t, J=4.1, 2H, CH═CH); 5.46; (dd, J=7.1, 4.6, 2H, C (3')); 4.81 (t, J=4.1, 4H, CO$_2$CH$_2$CH═CHCH$_2$CO$_2$); 1.59 (m, 1H, H—C(1")); 1.44 (m, 2H, H$_a$—C (2")); 1.16 (m, 2H, H$_b$—C (2")); 0.87 (d, J=6.8, 6H, Me-C(1")); 0.80 (t, J=7.4, 6H, H—C3")) ppm.
$^{13}$C-NMR (50 MHz, CDCl$_3$) δ: 165.1 (CONH); 163.8 (CO$_2$CH$_2$CH═CHCH$_2$CO$_2$); 151.2 (C(4')); 135.3 (C(4a')); 132.6, 130.7 (C(5') or C(6') or C(7')); 128.4, 128.2, 128.1 (C(8'), C(8a') C(CH═CH)); 123.8 (C(5') or C(6') or C(7')); 116.2 (C(2)); 59.9 (CO$_2$CH$_2$CH═CHCH$_2$CO$_2$); 55.9 (C(3')); 41.5 (C(1")); 24.5 (C(2")); 15.1 (Me-C(1")); 11.0 (C(3")) ppm.
MS (ES$^+$) m/e: 571 ([M+H]$^+$), 593 ([M+Na]$^+$), 1141 ([2M+H]$^+$), 1163 ([2M+Na]$^+$).

Example 11

Synthesis of (S,S,S,S,Z,Z)-(3-sec-butyl-1-oxo-2,3-dihydro-1H-isoquinolin-4-yliden)-but-2-inyl 4-[2-3-sec-butyl-1-oxo-2,3-dihydro-1H-isoquinolin-4-yliden)-acetoxyl]-acetate (13)

Following General Procedure I, compound 13 was obtained as a white solid (44 mg, 52% yield).

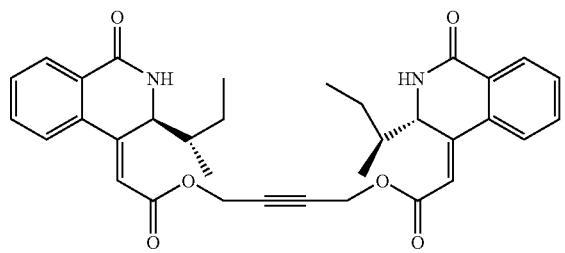

m.p.: 85-87° C.
$[\alpha]_D = -447.2$ (c=0.14 CHCl$_3$).
IR (KBr) v: 3434, 2963, 2927, 1718, 1669, 1378, 1273, 1152, 771 cm$^{-1}$.
$^1$H-NMR (300 MHz, CDCl$_3$) δ: 8.12 (m, 2H, H—C (8')); 7.55 (m, 6H, H—C (5'), H—C (6'), H—C (7')); 6.67 (broad d, J=4.5, 2H, NH); 6.35 (s, 2H, H—C(2)); 5.41 (dd, J=7.3, 4.5, 2H, C (3')); 4.82 (s, 4H, CO$_2$CH$_2$C≡CCH$_2$CO$_2$); 1.59 (m, 2H, H—C(1")); 1.42 (m, 2H, H$_a$—C (2")); 1.15 (m, 2H, H$_b$—C (2")); 0.85 (d, J=6.8, 6H, Me-C(1")); 0.77 (t, J=7.3, 6H, H—C3")) ppm.
$^{13}$C-NMR (75 MHz, CDCl$_3$) δ: 164.5 (CONH); 163.7 (CO$_2$CH$_2$C≡CCH$_2$CO$_2$); 152.1 (C(4')); 135.1 (C(4a')); 132.8, 130.9 (C(5') or C(6') or C(7')); 128.4 (C(8a')), 128.1 (C(8')); 123.9 (C(5') or (C(6') or C(7')); 115.6 (C(2)); 80.8 (CO$_2$CH$_2$C≡CCH$_2$CO$_2$); 56.1 (C(3')); 52.1 (CO$_2$CH$_2$C≡CCH$_2$CO$_2$); 41.6 (C(1")); 24.4 (C(2")); 15.1 (Me-C(1')); 11.1 (C(3")) ppm.
MS (ES$^+$) m/e: 569 ([M+H]$^+$), 591 ([M+Na]$^+$), 1137 ([2M+H]$^+$), 1159 ([2M+Na]$^+$).

Example 12

Synthesis of (S,S,S,S,Z,Z)-4-[2-(3-sec-butyl-1-oxo-2,3-dihydro-1H-isoquinolin-4-yliden)-acetoxyl]-benzyl (3-sec-butyl-1-oxo-2,3-dihydro-1H-isoquinolin-4-yliden)-acetate (14)

Following General Procedure I, compound 14 was obtained as a white solid (25 mg, 27% yield).

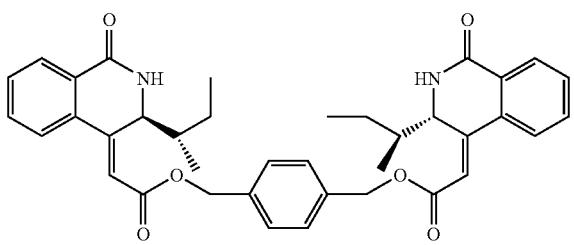

m.p.: 213-215° C.
$[\alpha]_D = -391.0$ (c=0.22, CHCl$_3$).

IR (KBr) v: 3422, 2927, 1712, 1671, 1379, 1275, 1158, 775 cm$^{-1}$.
$^1$H-NMR (300 MHz, CDCl$_3$) δ: 8.14 (m, 2H, H—C (8')); 7.57 (m, 6H, H—C (5'), H—C (6'), H—C (7')); 7.43 (s, 4H, CO$_2$CH$_2$PhCH$_2$CO$_2$); 6.40 (s, 2H, H—C (2)); 6.25 (broad d, J=4.7, 2H, NH); 5.45 (dd, J=7.1, 4.7, 2H, H—C (3')); 5.23 (s, 2H, CO$_2$CH$_2$PhCH$_2$CO$_2$); 5.22 (s, 2H, CO$_2$CH$_2$PhCH$_2$CO$_2$); 1.61 (m, 2H, H—C(1")); 1.44 (m, 2H, H$_a$—C (2")); 1.17 (m, 2H, H$_b$—C (2")); 0.87 (d, J=6.8, 6H, Me-C(1")); 0.81 (t, J=7.3, 6H, H—C3")) ppm.
$^{13}$C-NMR (75 MHz, CDCl$_3$) δ: 165.1 (CONH); 163.9 (CO$_2$CH$_2$PhCH$_2$CO$_2$); 151.3 (C(4')); 135.9 (C(Ph)); 135.3 (C(4a')); 132.7, 130.6 (C(5') or C(6') or C(7')); 128.5 (6 C, C(8a'), C(Ph)); 128.0 (C(8')); 123.8 (C(5') or C(6') or C(7')); 116.3 (C(2)); 65.8 (CO$_2$CH$_2$PhCH$_2$CO$_2$); 55.9 (C(3')); 41.5 (C(1")); 24.4 (C(2")); 15.1 (Me-C(1')); 11.0 (C(3")) ppm.
MS (ES$^+$) m/e: 621 ([M+H]$^+$), 643 ([M+Na]$^+$), 1241 ([2M+H]$^+$), 1264 ([2M+Na]$^+$).

Example 13

Reaction of the Acid 8 with Amines and Diamines (General Procedure II)

Synthesis of Amides of the Acid 8

To a suspension of the acid 8 (100 mg, 0.38 mmol) in anhydrous CH$_2$Cl$_2$ (2.5 mL) at 0° C. SOCl$_2$ was added (0.28 mL, 3.8 mmol) dropwise. The mixture was stirred until reaching room temperature and then heated at reflux for approximately 1 h. The solvent was then eliminated at reduced pressure obtaining a dark oil which was dissolved in anhydrous CH$_2$Cl$_2$ (2.5 mL), to which was added the corresponding amine (0.57 mmol of mono-amine or 0.17 mmol of di-amine) under argon, dissolved in anhydrous CH$_2$Cl$_2$ (2.5 mL). Et$_3$N was then added (0.1 mL, 0.76 mmol) and it was stirred at room temperature overnight. The reaction was then diluted with CH$_2$Cl$_2$ (50 mL) and was sequentially extracted with an aqueous solution of 5% HCl (3×50 mL) and a saturated aqueous solution of NaHCO$_3$ (3×50 mL). The organic phase was washed with brine and dried over MgSO$_4$. Once the solvent had been eliminated in vacuo the raw product was obtained, which was purified by column chromatography using hexane/EtOAc as eluent (7:3 to 1:1).

Example 14

Synthesis of (S,S,Z)-N-benzyl-2-(3-sec-butyl-1-oxo-2,3-dihydro-1H-isoquinolin-4-yliden)-acetamide (15)

Following General Procedure II, compound 15 was obtained as a white solid (119 mg, 90% yield).

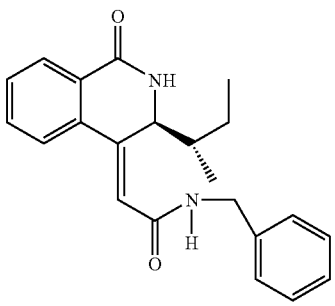

m.p.: 90-94° C.
[α]$_D$=−315.1 (c=0.25, CH$_3$OH).
IR (KBr) ν: 3435, 2963, 2927, 1651, 1523, 1450 cm$^{-1}$.
$^1$H-NMR (300 MHz, CDCl$_3$) δ: 8.10 (m, 1H, H—C (8')); 7.49 (m, 3H, H—C (5'), H—C (6'), H—C (7')); 7.32 (s, 5H, CONHCH$_2$Ph); 6.20 (broad s, J=4.5, 1H, NH); 6.17 (s, 1H, H—C (2)); 6.02 (m, 1H, CONHCH$_2$Ph); 5.65 (dd, J=7.3, 4.5, 2H, H—C(3')); 4.53 (m, 2H, CONHCH$_2$Ph); 1.63 (m, 1H, H—C (1")); 1.45 (m, 1H, H$_a$—(2")); 1.19 (m, 1H, H$_b$—C (2")); 0.89 (d, J=6.8, 3H, Me-C(1")); 0.81 (t, J=7.3, 3H, H—C(3")) ppm.
$^{13}$C-NMR (75 MHz, CDCl$_3$) δ: 164.7 (CONHCH$_2$Ph); 163.9 (CONH); 147.1 (C(4a')); 137.9 (C(4')); 135.9 (C(Ph)); 132.7, 129.9 (C(5') or C(6') or C(7')); 128.8, 128.4, 127.9, 127.7 (7 C, C(8'), C(8a'), C(Ph)); 123.5 (C(5') or C(6') or C(7')); 119.2 (C(2)); 55.6 (C(3')); 43.7 (CONHCH$_2$Ph); 41.3 (C(1")); 24.6 (C(2")); 15.2 (Me-C(1')); 11.1 (C(3")) ppm.
MS (ES$^+$) m/e: 349 ([M+H]$^+$), 371 ([M+Na]$^+$), 697 ([2M+H]$^+$), 719 ([2M+Na]$^+$).

Example 15

Synthesis of (S,S,Z)-N-(3-acetyl-phenyl)-2-(3-sec-butyl-1-oxo-2,3-dihydro-1H-isoquinolin-4-yliden)-acetamide (16)

Following General Procedure II, compound 16 was obtained as a white solid (112 mg, 79% yield).

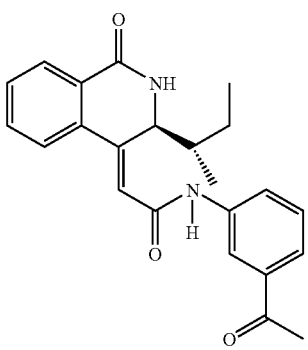

m.p.: 147-151° C.
[α]$_D$=−333.5 (c=0.26, CH$_3$OH).
IR (KBr) ν: 3413, 3435, 2964, 2927, 1673, 1656, 1549, 1484, 1167, 688 cm$^{-1}$.
$^1$H-NMR (500 MHz, 50° C., CDCl$_3$) δ: 8.33 (broad s, 1H, CONHAr); 8.10 (m, 2H, H—C (8') H—Ar); 7.98 (d, J=7.3, 1H, H—Ar); 7.66 (d, J=7.8, 1H H—Ar); 7.46 (m, 4H, H—C (5'), H—C (6'), H—C (7'), H—Ar); 6.51 (broad s, 1H, NH); 6.35 (s, 1H, H—C(2)); 5.60 (dd, J=7.3, 4.8, 2H, H—C(3')); 2.57 (s, 3H, ArCOCH$_3$); 1.63 (m, 1H, H—C (1")); 1.47 (m, 1H, H$_a$—C (2")); 1.15 (m, 1H, H$_b$—C (2")); 0.90 (d, J=6.8, 3H, Me-C(1")); 0.80 (t, J=7.3, 3H, H—C(3")) ppm.
$^{13}$C-NMR (75 MHz, CDCl$_3$) δ: 198.3 (ArCOCH$_3$); 164.5, 163.3 (CONH); 148.2 (C(4a')); 138.8 (C(4')); 135.9, 132.8, 130.2, 128.2, 127.8 (C(Ph), C(5') or C(6') or C(7'), C(8')); 129.(3 C(8a')); 124.4, 123.9 (C(2), C(Ph)); 55.6 (C(3')); 41.3 (C(1")); 29.7 (ArCOCH$_3$); 24.7 (C(2")); 15.2 (Me-C(1')); 11.2 (C(3")) ppm.
MS (ES$^+$) m/e: 377 ([M+H]$^+$), 399 ([M+Na]$^+$), 753 ([2M+H]$^+$), 775 ([2M+Na]$^+$).

Example 16

Synthesis of (S,S,Z)-N-(2'-amino-biphenyl-2-yl)-2-(3-sec-butyl-1-oxo-2,3-dihydro-1H-isoquinolin-4-yliden)-acetamide (17)

Following General Procedure II, compound 17 was obtained as a white solid (121 mg, 75% yield).

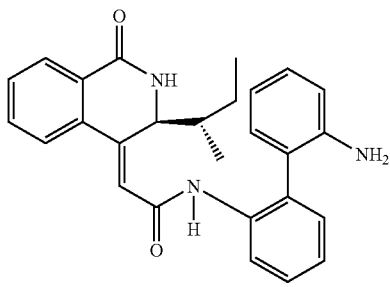

[α]$_D$=−312.6 (c=0.33, CH$_3$OH).
IR (KBr) ν: 3436, 1661, 1515, 1439, 1299, 1161, 749 cm$^{-1}$.
$^1$H-NMR (300 MHz, 30° C., CDCl$_3$, mixture of conformers M and m, 1:1) δ: 8.24 (m, 2H, H—Ar, M+m); 8.08 (m, 2H, H—C(8'), M+m); 8.00 (broad s, 1H, CONHAr, M); 7.95 (broad s, 1H, CONHAr, m); 7.54-7.39 (m, 8H, H—C (5'), H—C (6'), H—C (7'), H—Ar, M+m); 7.29-7.22 (m, 6H, H—Ar, M+m); 7.19-7.09 (m, 2H, H—Ar, M+m); 6.92-6.82 (m, 4H, H—Ar); 6.38 (broad s, 1H, NH, M); 6.38 (m, 1H, NH, m); 6.10 (s, 1H, H—C(2), M); 6.06 (s, 1H, H—C(2), m); 5.59 (m, 1H, H—C(3'), M); 5.33 (m, 1H, H—C(3'), m); 3.97 (s, 2H, ArNH$_2$, M+m); 1.59 (m, 1H, H—C(1"), M+m); 1.41 (m, 1H, H$_a$—C (2") M+m); 1.13 (m, 1H, H$_b$—C (2"), M+m); 0.85 (d, J=4.2, 3H, Me-C(1"), M); 0.83 (d, J=4.2, 3H, Me-C(1"), m); 0.77 (t, J=7.3, 3H, H—C(3")) ppm.
$^1$H-NMR (300 MHz, DMSO-d$_6$) δ: 9.32 (broad s, 1H, CONHAr); 8.48 (broad d, J=4.6, 1H, NH); 7.87 (m, 1H, H—C (8')); 7.70 (d, 1H, H—C (5')); 7.58 (m, 3H, H—C (6'), H—C (7'), H—C (2)); 7.37 (m, 1H, H—Ar) 7.25 (m, 2H, H—Ar); 7.06 (m, 1H, H—Ar); 6.92 (m, 1H, H—Ar); 6.78 (m, 1H, H—Ar); 6.64 (m, 1H, H—Ar); 6.56 (m, 1H, H—Ar); 5.43 (m, 1H, H—C(3')); 4.63 (s, 2H, ArNH$_2$); 1.35 (m, 2H, H$_a$—C (2"), H—C(1")); 1.21 (m, 1H, H$_b$—C (2")); 0.73 (m, 6H, Me-C(1"), H—C(3")) ppm.
$^{13}$C-NMR (300 MHz, CDCl$_3$, mixture of conformers M and m, 1:1) δ: 163.9, 163.8, 163.2 (CONH, M+m); 147.5, 147.1, 150.9, 137.8, 135.9, 132.7, 130.0, 128.8, 128.0, 127.9, 127.8 (19 C, C(4), C(4a'), C(5'), C(6'), C(7'), C(8a'), C(Ph), M+m); 125.2, 125.1 (C(Ar), M+m); 123.8, 123.7 (C(5') or C(6') or C(7'), M+m); 122.5, 122.3 (C(Ar), M+m); 120.3, 120.1, 119.7, 119.4, (C(2), C(Ar), M+m); 115.9

(C(Ar)); 55.9, 55.6 (C(3'), M+m); 41.4 (C(1")); 24.6 (C(2"));
15.2 (Me-C(1')); 11.2 (C(3")) ppm.

MS (ES$^+$) m/e: 426 ([M+H]$^+$), 753 ([2M+H]$^+$), 851 ([2M+H]$^+$), 874 ([2M+H+Na]$^+$).

Example 17

Synthesis of (S,S,S,S,Z,Z)-2,2'-bis-[(3-sec-butyl-1-oxo-2,3-dihydro-1H-isoquinolin-4-yliden)-acetylamino]biphenyl (18)

Following General Procedure II, compound 18 was obtained as a white solid (154 mg, 61% yield).

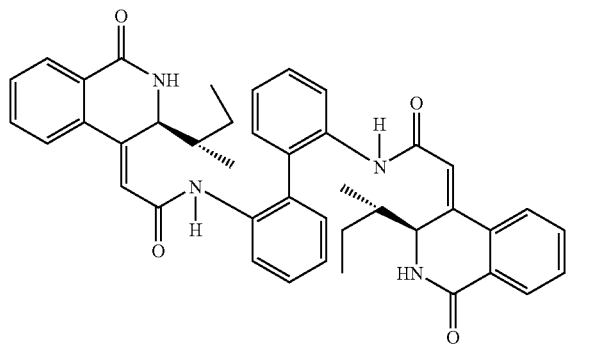

18 m.p.: 177-180° C.
[α]$_D$=−395.0 (c=0.25, CH$_3$OH).
IR (KBr) v: 3435, 2963, 1656, 1521, 1302, 1161, 753 cm$^{-1}$.
$^1$H-NMR (300 MHz, CDCl$_3$, mixture of conformers M and m, 1:1) δ: 8.10 (m, 2H, CONH-Bif, M+m); 8.06 (m, 1H, H—C(8'), M); 8.01 (m, 1H, H—C(8'), m); 7.52-7.16 (m, 14H, H—C(5'), H—C(6'), H—C(7'), H-Bif, M+m); 6.61 (broad d, 1H, NH-L-Biq, M); 6.36 (d, J=4.4, 1H, NH-L-Biq, m); 6.07 (s, 1H, H—C(2), M); 6.02 (s, 1H, H—C(2), m); 5.55 (m, 1H, H—C(3'), M); 5.37 (m, 1H, H—C(3'), m); 1.61-1.52 (m, 1H, H—C(1"), M+m); 1.38 (m, 1H, H$_a$—C (2"), M+m); 1.12 (m, 1H, H$_b$—C (2"), M+m); 0.86-0.71 (m, 12H, Me-C(1"), H—C (3"), M+m) ppm. [The acronym Biq is used for the isoquinoline derived radical and the acronym Bif for the biphenyl derivative].

MS (ES$^+$) m/e: 667 ([M+H]$^+$), 689 ([M+Na]$^+$), 1356 ([2M+H+Na]$^+$).

Example 18

Reaction of the Amine 17 with Amino Acid Derivatives (General Procedure III). Synthesis of Peptide-Heterocycle-Biphenyl Hybrids To a suspension of the corresponding N-Fmoc-amino acid (0.31 mmol) in anhydrous CH$_2$Cl$_2$ (2.0 mL) at 0° C., SOCl$_2$ was added (0.23 mL, 3.1 mmol) dropwise. The mixture was stirred until reaching room temperature and then heated at reflux for approximately 1 h. The solvent was then eliminated at reduced pressure obtaining a white solid which was dissolved in anhydrous CH$_2$Cl$_2$ (2.0 mL), to which was added the amine 17 (200 mg, 0.47 mmol) under argon, dissolved in anhydrous CH$_2$Cl$_2$ (2.0 mL). Et$_3$N was then added (80 μL, 0.62 mmol) and it was left stirring at room temperature overnight. The reaction was then diluted with CH$_2$Cl$_2$ (50 mL) and was sequentially extracted with an aqueous solution of NaHCO$_3$ (3×50 mL) and a saturated aqueous solution of 5% HCl (3×50 mL). The organic phase was washed with brine and dried over MgSO$_4$. Once the solvent had been eliminated in vacuo the raw product was obtained, which was purified by column chromatography using hexane/EtOAc as eluent (3:2 to 1:1).

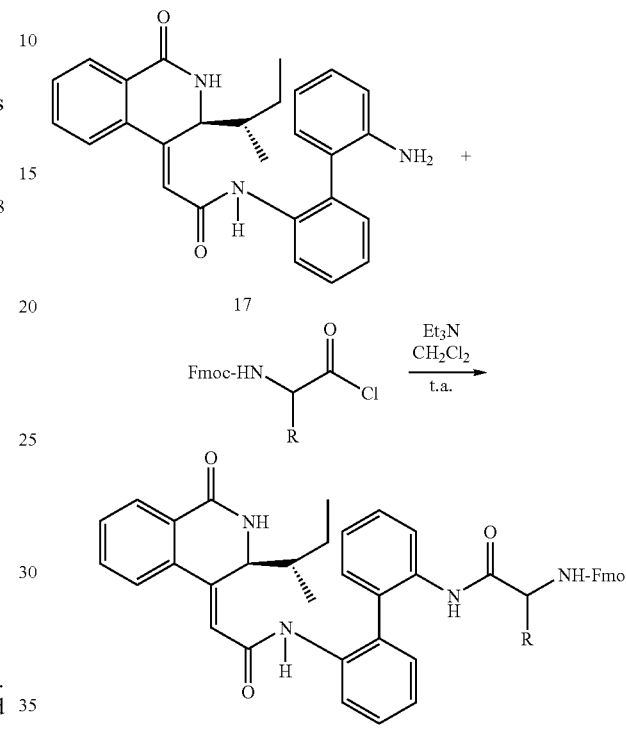

Example 19

Synthesis of (S,S,S,Z)-9H-fuorene-9-ylmethyl (1-{2'-[2-(3-sec-butyl-1-oxo-2,3-dihydro-1H-isoquinolin-4-yliden)-acetylamino]-biphenyl-2-ylcarbamoyl}-2-methyl-propyl)-carbamate (19)

Following General Procedure III, compound 19 was obtained as a white solid (172 mg, 73% yield).

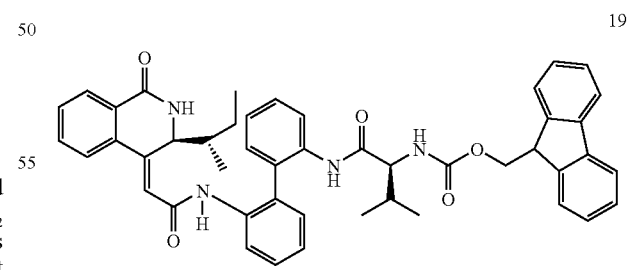

19 m.p.: 133-135° C.
[α]$_D$=−188.0 (c=0.25, CH$_2$Cl$_2$).
IR (KBr) v: 3408, 2963, 1663, 1519, 1450, 1299, 1232, 758, 739 cm$^{-1}$.
$^1$H-NMR (300 MHz, 323 K, CDCl$_3$, mixture of conformers M and m, 1:1) δ: 8.14-7.93 (m, 2H, H—Ar, M+m); 7.75-7.70 (m, 1H, H—Ar, M+m); 7.57-7.12 (m, 19H, H—Ar, CONH- Bif-CONH, M+m); 6.18 (d, J=4.4, 0.5H, NH-L-Biq, M); 6.12 (d, J=4.4, 0.5H, NH-L-Biq, m); 6.03 (s, 0.5H, H—C (2) M); 5.98 (s, 0.5H, H—C(2), m); 5.45 (m, 0.5H, H—C (3') M); 5.36 (s, 0.5H, H—C(3'), m); 5.04 (broad s, 1H, NH-Fmoc, M+m); 4.42-4.26 (m, 2H, CH$_2$—Fmoc, M+m), 4.17-4.09 (m, 1H, CH$_\alpha$-L-Val, M+m), 3.87 (m, 0.5H, CH-Fmoc, M), 3.81 (m, 0.5H, CH-Fmoc, m), 1.96 (m, 1H, CH$_\beta$-L-Val, M+m), 1.54 (m, 1H, H—C(1"), M+m); 1.40 (m, 1H, H$_a$—C (2"), M+m); 1.10 (m, 1H, H$_b$—C (2"), M+m); 0.89-0.73 (m, 12H, Me-C(1"), H—C(3"), Me$_2$ of L-Val, M+m) ppm.

$^1$H-NMR (300 MHz, 353 K, DMSO-d$_6$) δ: 8.93 (broad s, 1H, CONHBif); 8.75 (broad s, 1H, CONHBif); 8.14-6.94 (m, 22H, H—C (5') H—C (6'), H—C (7'), H—C (8'), H—Ar); 6.43 (s, 1H, H—C(2)); 5.34 (m, 1H, H—C(3')); 4.32-4.15 (m, 3H, CH$_2$—Fmoc, CH-Fmoc); 3.84 (m, 1H, CH$_1$-L-Val); 1.91 (m, 1H, CH$_\beta$-L-Val); 1.38 (m, 2H, H$_a$—C (2"), H—C(1")); 1.09 (m, 1H, H$_b$—C (2")); 0.86-0.66 (m, 12H, Me-C(1"), H—C(3"), Me$_2$ of L-Val) ppm.

MS (ES$^+$) m/e: 747 ([M+H]$^+$), 770 ([M+Na]$^+$), 1515 ([2M+H+Na]$^+$).

Example 20

Synthesis of (S,S,S,Z)-9H-fuorene-9-ylmethyl (1-{2'-[2-(3-sec-butyl-1-oxo-2,3-dihydro-1H-iso-quinolin-4-yliden)-acetylamino]-biphenyl-2-ylcarbamoyl}-2-phenyl-ethyl)-carbamate (20)

Following General Procedure III, compound 20 was obtained as a white solid (109 mg, 45% yield).

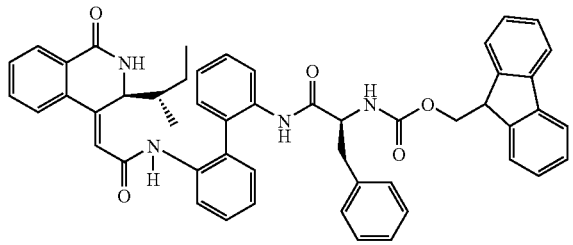

20 m.p.: 108-110° C.

[α]$_D$=−181.0 (c=0.23, CH$_2$Cl$_2$).

IR (KBr) v: 3409, 2956, 1659, 1519, 1450, 1247, 1161, 1046, 758, 739 cm$^{-1}$.

$^1$H-NMR (300 MHz, 313 K, CDCl$_3$, mixture of conformers M and m, 1.5:1) δ: 8.14-7.99 (m, 2H, H—Ar, M+m); 7.88-7.65 (m, 3H, H—Ar, M+m); 7.48-7.01 (m, 20H, H—Ar, M+m); 6.72 (d, J=4.4, 0.6H, NH-L-Biq, M); 6.52 (d, J=4.4, 0.4H, NH-L-Biq, m); 6.05 (s, 0.6H, H—C (2), M); 5.98 (s, 0.4H, H—C(2), m); 5.46 (m, 0.4H, H—C (3') m); 5.37 (s, 0.4H, H—C(3'), M); 5.27 (broad s, 0.6H, NH-Fmoc, M); 5.02 (broad s, 0.4H, NH-Fmoc, m); 4.38-4.06 (m, 4H, CH$_2$—Fmoc, CH-Fmoc, CH$_1$-L-Phe, M+m), 3.21 (m, 1H, CH-L-Phe, M), 2.84 (m, 1H, CH$_\beta$-L-Phe, m); 1.61 (m, 1H, H—C (1"), M+m); 1.41 (m, 1H, H$_a$—C (2"), M+m); 1.13 (m, 1H, H$_b$—C (2"), M+m); 0.80 (d, 2H, J=6.8, Me-C(1"), M); 0.80 (d, 0.5H, J=6.8, Me-C(1"), m); 0.74 (t, 3H, J=7.8, H—C(3"), M+m) ppm.

MS (ES$^+$) m/e: 795 ([M+H]$^+$), 818 ([M+Na]$^+$), 1612 ([2M+H+Na]$^+$).

Example 21

Synthesis of (S,S,S,S,Z)-9H-fuorene-9-ylmethyl (1-{2'-[2-(3-sec-butyl-1-oxo-2,3-dihydro-1 H-iso-quinolin-4-yliden)-acetylamino]-biphenyl-2-ylcarbamoyl}-2-methyl-butyl)-carbamate (21)

Following General Procedure III, compound 21 was obtained as a white solid (101 mg, 58% yield).

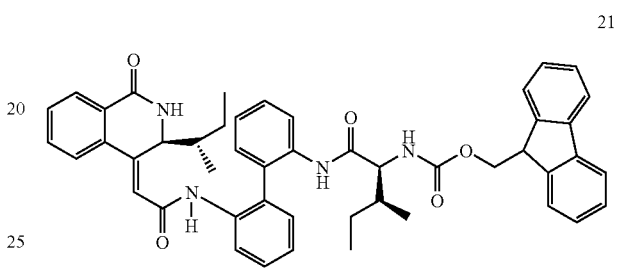

21 m.p.: 116-120° C.

[α]$_D$=−155.1 (c=0.12, CHCl$_3$).

IR (KBr) v: 3406, 3282, 2963, 2920, 1662, 1516, 1450, 1233, 757, 740 cm$^{-1}$.

$^1$H-NMR (300 MHz, 318 K, CDCl$_3$, mixture of conformers M and m, 1:1) δ: 8.12-7.01 (m, 22H, H—Ar, CONH-Bif-CONH, M+m); 6.33 (broad s, 0.5H, NH-L-Biq, M); 6.27 (broad s, 0.5H, NH-L-Biq, m); 6.05 (s, 0.5H, H—C (2) M); 5.99 (s, 0.5H, H—C(2), m); 5.47 (m, 0.5H, H—C (3') M); 5.34 (s, 0.5H, H—C(3'), m); 5.23 (broad s, 1H, NH-Fmoc, M+m); 4.44-3.88 (m, 4H, CH$_2$—Fmoc, CH-Fmoc, CH$_\alpha$-L-Ile, M+m), 1.86 (m, 0.5H, CH$_\beta$-L-Ile, M); 1.72 (m, 0.5H, CH$_\beta$-L-Ile, m), 1.54 (m, 1H, H—C(1"), M+m); 1.40 (m, 1H, H$_a$—C (2"), M+m); 1.14 (m, 1H, H$_b$—C (2"), CH$_b$-L-Ile, M+m); 0.88-0.70 (m, 12H, Me-C(1"), H—C(3"), [CH—CH$_3$] of L-Ile, [CH$_2$—CH$_3$] of L-Ile, M+m) ppm.

MS (ES$^+$) m/e: 761 ([M+H]$^+$), 783 ([M+Na]$^+$), 1522 ([2M+H]$^+$), 1545 ([2M+Na]$^+$).

Example 22

Deprotection of the N-Fmoc Group (General Procedure IV)

To a solution of the corresponding protected N-Fmoc compound (0.09 mmol) in 0.3 mL of anhydrous DMF at 0° C. piperidine was added (70 μL) under argon. The mixture was then left to reach room temperature for 2 h. Once the solvent had been eliminated the raw product was obtained, which was purified by column chromatography using hexane/EtOAc as eluent (1:1 to 1:9).

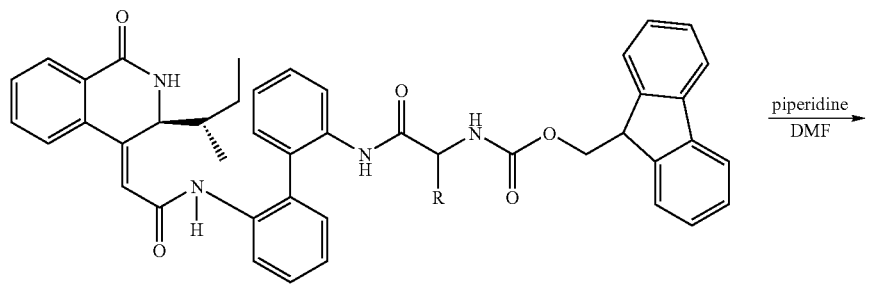

Example 23

Synthesis of (S,S,S,Z)-2-amino-N-{2'-[2-(3-sec-butyl-1-oxo-2,3-dihydro-1H-isoquinolin-4-yliden)-acetylamino]-biphenyl-2-yl}-3-methyl-butyramide (22)

Following General Procedure IV, compound 22 was obtained as a white solid (12 mg, 24% yield).

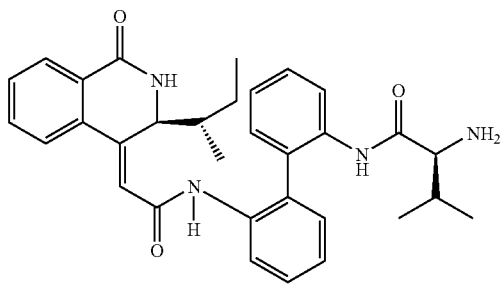

m.p.: 110-113° C.
$[\alpha]_D = -35.9$ (c=0.07, CHCl$_3$).
IR (KBr) ν: 3434, 2956, 1660, 1521, 14369, 1165, 753 cm$^{-1}$.
$^1$H-NMR (500 MHz, 313 K, CDCl$_3$, mixture of conformers M and m, 1:1) δ: 9.31 (broad s, 0.5H, CONH-Bif-CONH, M); 9.28 (broad s, 0.5H, CONH-Bif-CONH, m); 8.38 (broad s, 0.5H, CONH-Bif-CONH, M); 8.28 (broad s, 0.5H, CONH-Bif-CONH, m); 8.09 (m, 1H, H—C(8'), M); 8.19 (m, 1H, H—C(8'), m); 7.45 (m, 6H, H—Ar. H-Bif M+m); 7.23 (m, 5H, H—Ar. H-Bif M+m); 6.25 (d, J=4.5, 0.5H, NH-L-Biq, M); 6.18 (d, J=4.5, 0.5H, NH-L-Biq, m); 6.03 (s, 0.5H, H—C(2) M); 5.99 (s, 0.5H, H—C(2), m); 5.52 (m, 0.5H, H—C (3') M+m); 3.47 (m, 1H, NH$_2$, M); 3.29 (m, 1H, NH$_2$, m); 3.23 (d, J=3.4, 0.5H, CHa-L-Val, M); 3.15 (d, J=3.4, 0.5H, CH$_1$-L-Val, m), 2.24 (m, 1H, CH$_\beta$-L-Val, M+m); 1.61 (m, 1H, H—C (1"), M+m); 1.52 (m, 1H, H$_a$—C (2"), M+m); 1.18 (m, 1H, H$_b$—C (2"), M+m); 0.91-0.63 (m, 12H, Me-C(1"), H—C (3"), Me$_2$ of L-Val, M+m) ppm.

MS (ES$^+$) m/e: 525 ([M+H]$^+$), 547 ([M+Na]$^+$), 1049 ([2M+H]$^+$), 1072 ([2M+Na]$^+$).

Example 24

Synthesis of (S,S,S,Z)-2-amino-N-{2'-[2-(3-sec-butyl-1-oxo-2,3-dihydro-1H-isoquinolin-4-yliden)-acetylamino]-biphenyl-2-yl}-3-phenyl-propionamide (23)

Following General Procedure IV, compound 23 was obtained as a white solid (32 mg, 61% yield).

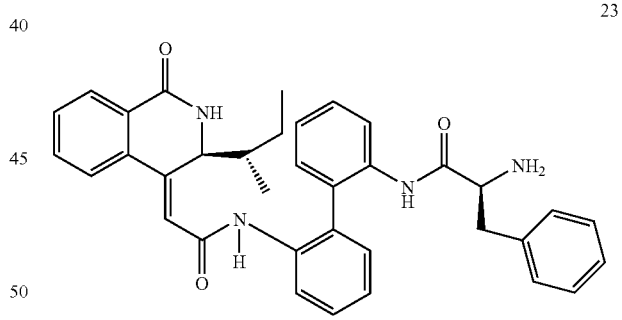

m.p.: 107-110° C.
$[\alpha]_D = -231.0$ (c=0.06, CH$_2$Cl$_2$).
IR (KBr) ν: 3435, 1658, 1519, 1436, 1161, 753 cm$^{-1}$.
$^1$H-NMR (500 MHz, CDCl$_3$, mixture of conformers M and m, 2.5:1) δ: 9.36 (broad s, 0.7H, CONH-Bif-CONH, M); 9.32 (broad s, 0.3H, CONH-Bif-CONH, m); 8.40-8.05 (m, 3H, H—C(8'), CONH-Bif-CONH, M+m); 7.53-7.44 (m, 6H, H—Ar, H-Bif, M+m); 7.43-7.13 (m, 5H, H—Ar, H-Bif, M+m); 6.49 (m, 1H, NH-L-Biq, M+m); 6.07 (s, 0.7H, H—C(2) M); 6.06 (s, 0.3H, H—C(2), m); 5.51 (m, 1H, H—C (3') M+m); 3.55 (m, 1H, CH$_\alpha$-L-Phe, M+m); 3.18 (m, 1H, CH$_\beta$-L-Phe, M+m); 2.49 (m, 1H, CH-L-Phe, m); 1.59 (m, 1H, H—C (1"), M+m); 1.50 (m, 1H, H$_a$—C (2"), M+m); 1.16 (m, 1H, H$_b$—C (2"), M+m); 0.90-0.70 (m, 6H, Me-C(1"), H—C(3"), M+m) ppm.

Example 25

Synthesis of (S,S,S,S,Z)-2-amino-N-{2'-[2-(3-sec-butyl-1-oxo-2,3-dihydro-1H-isoquinolin-4-yliden)-acetylamino]-biphenyl-2-yl}-3-methyl-pentanamide (24)

Following General Procedure IV, compound 24 was obtained as a white solid (34 mg, 71% yield).

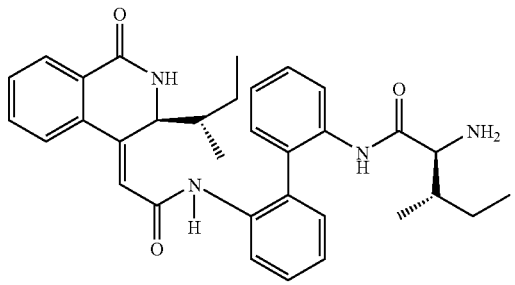

m.p.: 93-96° C.

$[\alpha]_D = -215.6$ (c=0.09, MeOH).

IR (KBr) v: 3413, 2962, 2920, 1666, 1580, 1521, 1436, 1302, 1164, 755 cm$^{-1}$.

$^1$H-NMR (400 MHz, CDCl$_3$, mixture of conformers M and m, 1:1) δ: 9.41 (broad s, 0.5H, CONH-Bif-CONH, M); 9.38 (broad s, 0.5H, CONH-Bif-CONH, m); 8.32 (broad s, 0.5H, CONH-Bif-CONH, M); 8.22 (broad s, 0.5H, CONH-Bif-CONH, m); 8.13 (m, 0.5H, H—C(8'), M); 8.03 (m, 0.5H, H—C(8'), m); 7.46-7.35 (m, 6H, H—Ar, H-Bif, M+m); 7.24-7.09 (m, 5H, H—Ar, H-Bif, M+m); 6.77 (d, J=4.4, 0.5H, NH-L-Biq, M+m); 6.70 (d, J=4.4, 0.5H, NH-L-Biq, M+m); 6.04 (s, 0.5H, H—C (2), M); 6.02 (s, 0.5H, H—C(2), m); 5.48 (m, 1H, H—C (3') M+m); 3.26 (m, J=3.4, 0.5H, CHa-L-Ile, M); 3.17 (m, J=3.4, 0.5H, CH$_\alpha$-L-Ile, m); 1.96 (m, 1H, CH-L-Ile, M); 1.88 (m, 1H, CH$_\beta$-L-Ile, m); 1.58 (m, 1H, H—C(1"), M+m); 1.52 (m, 1H, H$_a$—C (2"), M+m); 1.14 (m, 1H, H$_b$—C (2"), M+m); 0.89-0.74 (m, 12H, Me-C(1"), H—C(3"), [CH—CH$_3$] of L-Ile, [CH$_2$—CH$_3$] of L-Ile, M+m) ppm.

Example 26

Synthesis of Peptide-isoquinoline Hybrids (General Procedure V)

To a solution of the acid 8 (150 mg, 0.58 mmol) in anhydrous DMF was sequentially added the corresponding peptide (as trifluoroacetate) (0.70 mmol), 1-hydroxybenzotriazol (HOBT, 92 mg, 0.70 mmol), 1-(3-dimethylaminopropyl)-3-ethylcarbodiimade (EDC, 134.4 mg, 0.70 mmol) and 4-(dimethylamino) pyridine (DMAP, 7 mg, 0.058 mmol). The mixture was stirred at room temperature overnight. The organic solvent was then eliminated in vacuo and the raw product was purified by column chromatography to give the corresponding peptide-isoquinoline hybrid.

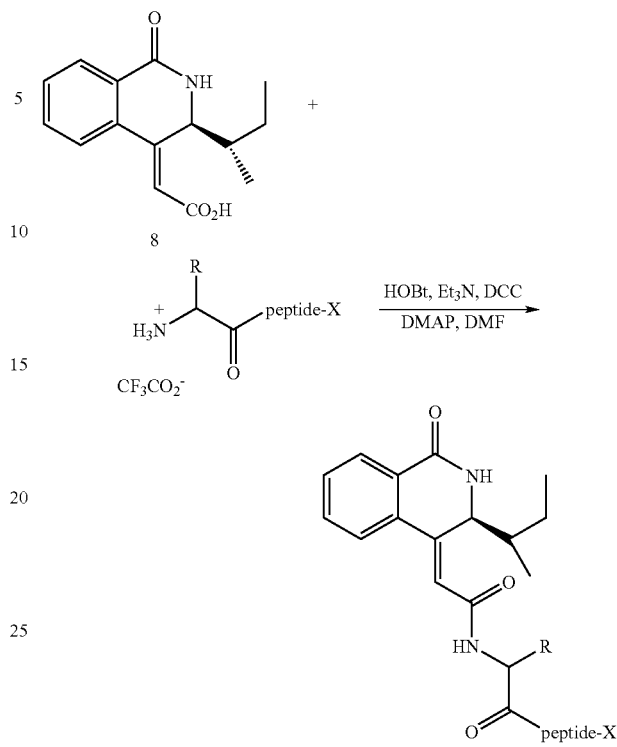

Example 27

Synthesis of methyl (S,S,S,S,Z)-2-{2-[2-(3-sec-butyl-1-oxo-2,3-dihydro-1H-isoquinolin-4-yliden)-acetylamino]-3-methyl-pentanoylamino}-3-methyl-pentanoate (25)

Following General Procedure V, starting from the peptide CF$_3$CO$_2^-$-+H-L-Ile-L-Ile-OCH$_3$, and following purification by chromatography (mixtures of hexane-EtOAc 4:1 to 3:2), the compound 25 was obtained as a white solid (232 mg, 80% yield).

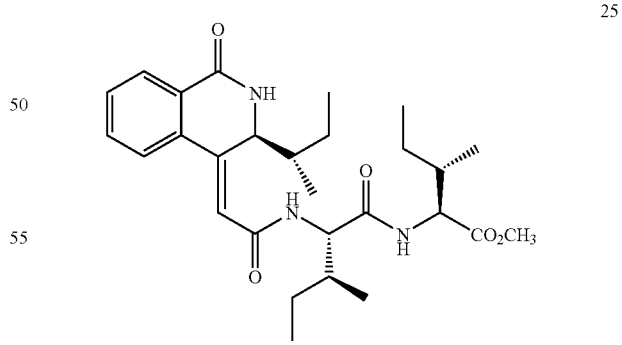

IR (KBr) v: 3436, 2965, 1743, 1652, 1544 cm$^{-1}$.

$^1$H-NMR (300 MHz, CDCl$_3$,) δ: 8.26 (m, J=5.1, 1H, NH-L-11q); 7.96 (m, 1 H—C(8')); 7.38-7.21 (m, 5H H—C (5'), H—C (6'), H—C (7'), NH-L-Ile [1], NH-L-Ile [2]); 6.09 (s, 1H, olefinic H); 5.57 (dd, J=7.2, 5.1, 1H, H—C(3')); 4.68 (m, 1H, CH$_\alpha$-L-Ile [2]); 4.43 (dd, J=7.6, 5.1, 1H, CH$_\alpha$-L-Ile [1]); 3.72 (s, 3H, CO$_2$Me); 1.93-1.79 (m, 3H, [Me-CH-Et] of L-liq;

CH$_\beta$-L-Ile [1], CH-L-Ile [2]); 1.66-1.08 (m, 6H, [Me-CH—CH$_2$CH$_3$] of L-liq, [Me-CH—CH$_2$CH$_3$] of L-liq, [CH—CH$_3$] of L-Ile [1], [CH—CH$_3$] of L-Ile [2], [CH$_2$CH$_3$] of L-Ile [1], [CH$_2$CH$_3$] of L-Ile [2] ppm.

$^{13}$C-NMR (50 MHz, CDCl$_3$) δ: 172.0, 171.9 (CO$_2$Me, CONH— L-Ile [2]); 164.8, 164.5 (=C—CONH, CONH— L-Liq), 147.5 (C(4')), 136.0 (C(4a')), 132.4, 129.5, 123.6 (C(5'), C(6'), C(7'), 128.3 (C(8a')); 127.5 (C(8)); 119.2 (olefinic CH); 57.3 (CH$_\alpha$-L-Ile [2]); 56.9 (CH$_\alpha$-L-Ile [1]); 54.9 (C(3')); 51.9 (CO$_2$Me); 41.3, 38.3, 37.1 ([Me-CH-Et] of L-liq; CH$_\beta$-L-Ile [1], CH-L-Ile [2]); 25.1, 24.9 (3 C [Me-CH—CH$_2$CH$_3$] of L-liq, CH$_2$-L-Ile [1], CH$_2$ of L-Ile [2]); 15.4, 15.3, 15.0, 11.4, 11.2 ((6 C [Me-CH—CH$_2$CH$_3$] of L-liq, [Me-CH—CH$_2$CH$_3$] of L-liq, [CH—CH$_3$] of L-Ile [1]), [CH—CH$_3$] of L-Ile [2], [CH$_2$—CH$_3$] of L-Ile [1], [CH$_2$—CH$_3$] of L-Ile [2]) ppm.

MS (ES$^+$) m/e: 500 ([M+H]$^+$), 522 ([M+Na]$^+$), 999 ([2M+H]$^+$), 1021 ([2M+Na]$^+$).

Example 28

Synthesis of methyl (S,S,S,S,S,S,S,S,S,Z)-2-(2-{2-[2-(3-sec-butyl-1-oxo-2,3-dihydro-1H-isoquinolin-4-yliden)-acetylamino]-3-methyl-pentanoylamino}-3-methyl-pentanoylamino)-3-methyl-pentanoate (26)

Following General Procedure V, starting from the peptide CF$_3$CO$_2$-+H-L-Ile-L-Ile-OCH$_3$, and following purification by chromatography (mixtures of hexane-EtOAc 1:4 to 1:9), the compound 26 was obtained as a white solid (234 mg, 66% yield).

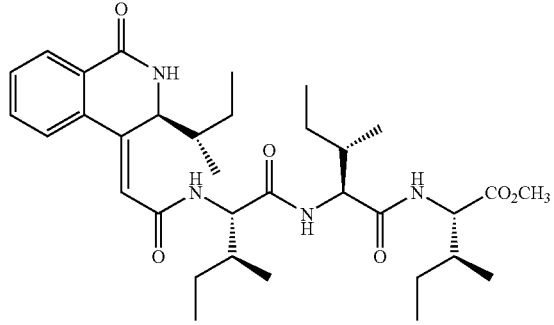

26 m.p.: 151-154° C.
[α]$_D$=−100.9 (c=0.33, MeOH).
IR (KBr) v: 3302, 2965, 1739, 1650, 1529, 1207 cm$^{-1}$.
$^1$H-NMR (300 MHz, (D$_6$)DMSO) δ: 8.49 (d, J=4.5, 1H, NH-L-Biq); 8.25 (d, J=8.5, 1H NH-L-Ile [3]); 8.14 (d, J=7.3, 1H NH-L-Ile [1]); 7.99 (d, J=8.7, 1H NH-L-Ile [2]); 7.88 (dd, J=7.3, 0.8, 1H, H—C(8')); 7.66-7.58 (m, 2H H—C(5'), H—C(6'), H—C(7'); 7.50 (td, J=7.6, 0.9, 1H, H—C(7')); 6.70 (s, 1H, olefinic H); 5.47 (dd, J=7.3, 4.5, 1H, H—C(3')); 4.35 (t, J=8.5, 1H, CH$_\alpha$-L-Ile [3]); 4.24 (t, J=8.7, 1H, CH$_\alpha$-L-Ile [2]); 4.17 (t, J=7.3, 1H, CH$_\alpha$-L-Ile [1]); 3.58 (s, 3H, CO$_2$Me); 1.84-1.62 (m, 3H, CH-L-Ile [1], CH-L-Ile [2], CH-L-Ile [3]); 1.52-0.91 (m, 9H, [Me-CH-Et] of L-Biq, [Me-CH—CH$_2$CH$_3$] of L-Biq, CH$_2$-L-Ile [1], CH$_2$-L-Ile [2], CH$_2$-L-Ile [3]); 0.90-0.68 (m, 24H, [Me-CH—CH$_2$CH$_3$] of L-Biq, [Me-CH—CH$_2$CH$_3$] of L-Biq, [CH—CH$_3$] of L-Ile [1], [CH—CH$_3$] of L-Ile [2], [CH—CH$_3$] of L-Ile [3], [CH$_2$—CH$_3$] of L-Ile [1], [CH$_2$—CH$_3$] of L-Ile [2] [CH$_2$—CH$_3$] of L-Ile [3]) ppm.

$^{13}$C-NMR (50 MHz, (D$_6$)DMSO) δ: 171.7, 171.2, 170.7 (CONH-L-Ile [1], CONH-L-Ile [2], =CH—CONH); 164.6, 162.6 (CONH— L-Biq, CO$_2$Me); 144.0 (C(4')), 136.0 (C(4a')), 132.4 (C(5') or C(6'); 129.5 (C(7'), 128.6 (C(8a')); 126.9 (C(8')); 123.7 (C(5') or C(6'); 120.3 (olefinic CH); 56.5, 56.4, 56.2 (CH$_\alpha$-L-Ile [1], CH$_\alpha$-L-Ile [2], CH$_\alpha$-L-Ile [3]); 54.6 C(3')); 51.5 (CO$_2$Me); 41.3 [Me-CH-Et] of L-Biq]; 36.8, 36.5, 35.9 (CH-L-Ile [1], CH-L-Ile [2], CH$_\beta$-L-Ile [3]); 24.6, 24.2 (4 C [Me-CH—CH$_2$CH$_3$] of L-Biq, CH$_2$-L-Ile [1], CH$_2$-L-Ile [2], CH$_2$-L-Ile [3]); 15.3, 15.2, 15.0, 14.9, 11.0, 10.9, 10.8 (8 C [Me-CH—CH$_2$CH$_3$] of L-Biq, [Me-CH—CH$_2$CH$_3$] of L-Biq, [CH—CH$_3$] of L-Ile [1], [CH—CH$_3$] of L-Ile [2], [CH—CH$_3$] of L-Ile [3], [CH$_2$—CH$_3$] of L-Ile [1], [CH$_2$—CH$_3$] of L-Ile [2] [CH$_2$—CH$_3$] of L-Ile [3]) ppm.

MS (ES$^+$) m/e: 613 ([M+H]$^+$), 635 ([M+Na]$^+$), 1226 ([2M+H]$^+$), 1247 ([2M+Na]$^+$).

Example 29

Synthesis of methyl (S,S,S,S,Z)-2-{2-[2-(3-sec-butyl-1-oxo-2,3-dihydro-1H-isoquinolin-4-yliden)-acetylamino]-3-methyl-butirylamino}-3-phenyl-propionate (27)

Following General Procedure V, starting from the peptide CF$_3$CO$_2$-+H-L-Val-L-Phe-OCH$_3$, and following purification by chromatography (mixtures of hexane-EtOAc 3:2 to 2:3), the compound 27 was obtained as a white solid (217 mg, 72% yield).

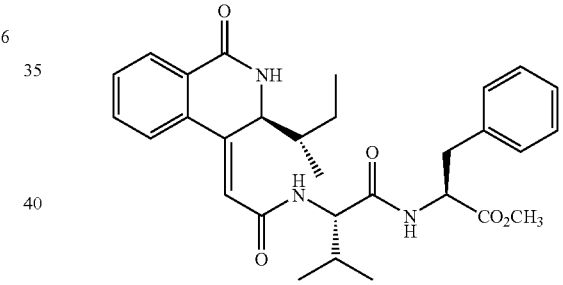

27 m.p.: 174-176° C.
[α]$_D$=−129.0 (c=0.5 CHCl$_3$).
IR (KBr) v: 3436, 2964, 1743, 1655, 1538 cm$^{-1}$.
$^1$H-NMR (400 MHz, CDCl$_3$) δ: 8.24(d, J=4.6, 1H, NH-L-Biq); 7.96 (dd, J=7.6, 1.4, 1H, H—C(8')); 7.37-7.03 (m, 10H, H—C(5'), H—C(6'), H—C(7'), NH-L-Ile, NH-L-Phe, aromatic of L-Phe); 6.06 (s, 1H, olefinic H); 5.57 (dd, J=9.1, 4.9, 1H, H—C(3')); 4.74 (dd, J=14.0, 6.3, 1H, CHa-L-Phe); 4.48 (dd, J=9.1, 6.6, CH$_\alpha$-L-Val); 3.66 (s, 3H, CO$_2$Me); 2.91 (dd, J=14.0, 6.3, 2H, CH$_\beta$-L-Phe); 2.11 (m, 1H, CH$_\beta$-L-Val); 1.57-1.48 (m, 2H, [Me-CH—CH$_2$CH$_3$] of L-Biq,); 1.17-1.09 (m, 1H, [Me-CH—CH$_2$CH$_3$] of L-Biq); 1.00 (d, J=6.7, 3H, Me$_2$ of L-Val); 0.96 (d, J=6.7, 3H, Me$_2$ of L-Val); 0.85 (d, J=6.7, 3H, [Me-CH—CH$_2$CH$_3$] of L-Biq); 0.80 (t, J=7.3, 3H, [Me-CH—CH$_2$CH$_3$] of L-Biq) ppm.

$^{13}$C-NMR (50 MHz, CDCl$_3$) δ: 1712.0, 171.5 (CONH-L-Val, CO$_2$Me); 164.9, 164.6 (=CH—CONH, CONH-L-Biq); 147.2 (C(4')), 135.9, 135.7, 132.5, 129.6, 129.2, 128.5, 128.3, 127.4, 127.0, 123.6 (12 C, C(4a'), (C(5'), C(6'), C(7'), C(8a'), C(8'), aromatic C of L-Phe): 119.1 (olefinic CH); 58.3 (CHa-L-Phe); 55.0 (C(3')); 53.3 (CHa-L-Val); 52.1 (CO$_2$Me); 41.3 [Me-CH—CH$_2$CH$_3$] of L-Biq), 37.5 (CH$_\beta$-L-Phe); 31.6 (CH$_\beta$-L-Val); 24.7 ([Me-CH—CH$_2$CH$_3$] of L-Biq, 19.2, 18.2

(Me₂ of L-Val); 15.1 ([Me-CH—CH₂CH₃] of L-Biq); 11.3 ([Me-CH—CH₂CH₃] of L-Biq) ppm.

MS (ES⁺) m/e: 520 ([M+H]⁺), 542 ([M+Na]⁺), 1039 ([2M+H]⁺), 1061 ([2M+Na]⁺).

Example 30

Synthesis of methyl (S,S,Z)-(3-sec-butyl-1-thioxo-2,3-dihydro-1H-isoquinolin-4-yliden)-acetate (28)

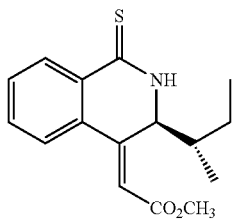

28

To a solution of isoquinolinone 7 (273 mg, 1.0 mmol) in anhydrous toluene (9.0 mL), Lawesson's reagent ([2,4-bis(4-methoxyphenyl)-1,3-dithia-2,4-diphosphetane-2,4-disulphide]) was added (445 mg, 1.1 mmol) and the mixture was refluxed for approximately 1 h. The mixture was then left to reach room temperature and the solvent was eliminated in vacuo obtaining a raw product, which was purified by column chromatography using hexane/EtOAc as eluent (19:1 to 7:3), giving 263 mg (91% yield) of 27, as a yellow solid.

m.p.: 50-53° C.

$[\alpha]_D$=−754.2 (c=0.5, CHCl₃).

IR (KBr) v: 3436, 3432, 3170, 2665, 1713, 1637, 1368, 1215, 1195, 1172, 1013, 772 cm⁻¹.

¹H-NMR (300 MHz, 50° C., CDCl₃) δ: 8.58 (broad s, 1H, NH); 8.58 (dd, J=7.5, 1.7, 1H, H—C(8')); 7.55-7.43 (m, 3H, H—C(5'), H—C(6'), H—C(7')), 6.31 (s, 1H, H—C(2')); 5.48 (dd, J=7.8, 5.1, 1H, H—C(3')); 3.75 (s, 3H, CO₂Me); 1.66 (m, 1H, H—C (1")); 1.49 (m, 1H, H$_a$—C (2")); 1.19 (m, 1H, H$_b$—C (2")); 0.86-0.79 (m, 6H, Me-C(1"), H—C(3")) ppm.

¹³C-NMR (50 MHz, CDCl₃) δ: 191.4 (CSNH); 165.8 (CO₂Me); 149.6 (C(4')); 133.1 (C(4a')); 132.3, 131.0 (C(5') or C(6') or C(7')); 130.8 (C(8a')); 130.5 (C(8')); 123.7 (C(5') or C(6') or C(7')); 117.1 C(2')); 57.7 (C(3')); 51.7 (CO₂Me); 40.8 (C(1")); 24.9 (C(2")); 14.9, 10.9 (Me-C(1')) C(3")) ppm.

MS (ES⁺) m/e: 290 ([M+H]⁺), 312 ([M+Na]⁺), 601 ([2M+Na]⁺).

Example 31

Synthesis of (S,S,Z)-(3-sec-butyl-1-thioxo-2,3-dihydro-1H-isoquinolin-4-yliden)-acetic acid (29)

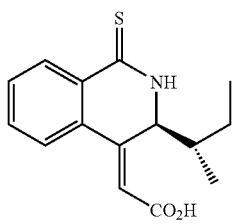

29

To a solution of thiolactame 27 (231.2 mg, 0.8 mmol) in a 1:1 mixture of THF—H₂O (8 mL) at room temperature, a solution of LiOH (1.6 mmol) in H₂O (1.6 mL) was added. The mixture was stirred at room temperature overnight and then acidified with 5% HCl to pH=2. The THF was eliminated in vacuo and the aqueous phase was extracted with EtOAc (3×50 mL). The organic phases were washed with brine and dried over MgSO₄. Once the solvent had been eliminated in vacuo the raw product was obtained, which was purified by recrystallisation of EtOAc/hexane in order to give the acid 28 (211 mg, 96% yield) as a yellow solid.

m.p.: 193-196° C.

$[\alpha]_D$=−600.5 (c=0.5, CH₃OH).

IR (KBr) v: 3449, 3210, 2963, 1674, 1281, 1254, 1219, 776 cm⁻¹.

¹H-NMR (300 MHz, DMSO-d₆) δ: 12.77 (broad s, 1H, CO₂H); 11.03 (d, J=4.9, 1 NH); 8.39 (dd, J=7.6, 1H, H—C (8')); 7.72-7.53 (m, 3H, H—C (5'), H—C (6'), H—C (7')), 6.39 (s, 1H, H—C(2)); 5.33 (dd, J=8.2, 4.9, 1H, H—C(3')); 1.56-1.46 (m, 1H, H$_a$—C (2")); 1.44-1.38 (m, 1H, H—C(1')); 1.19-1.06 (m, 1H, H$_b$—C (2")); 0.78 (t, J=7.5, 3H, Me-C(1")); 0.81 (d, J=6.9, 3H, H—C(3")) ppm.

¹³C-NMR (50 MHz, DMSO-d₆) δ: 189.3 (CSNH); 166.6 (CO₂H); 147.8 (C(4')); 133.1 (C(4a')); 131.1 (2 C, C(5') or C(6') or C(7')); 130.6 (C(8a')); 130.1 (C(8')); 124.4 (C(5') or C(6') or C(7')); 118.8 (C(2)); 55.7 (C(3')); 40.9 (C(1")); 24.8 (C(2")); 14.9 (Me-C(1')); 10.9 (C(3")) ppm.

MS (ES⁺) m/e: 276 ([M+H]⁺), 298 ([M+Na]⁺), 573 ([2M+Na]⁺).

Example 32

Synthesis of methyl (S,S,S,S,S,S,Z)-2-{2-[2-(3-sec-butyl-1-thioxo-2,3-dihydro-1H-isoquinolin-4-yliden)-acetylamino]-3-methyl-pentanoylamino}-3-methyl-pentanoate (30)

The compound was obtained following General Procedure V, starting from the acid 29 and the peptide CF₃CO₂-+H-L-Ile-L-Ile-OCH₃. It was purified by chromatography using mixtures of hexane/EtOAc (4:1 to 3:2) in order to give 30 as an oil (257 mg, 86% yield).

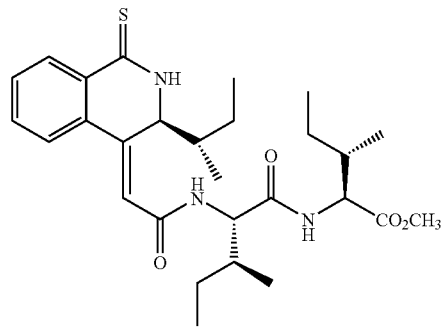

30 m.p.: 178-181° C.

$[\alpha]_D$=−366.0 (c=0.25, CHCl₃).

IR (KBr) v: 3435, 2964, 1739, 1631, 1525, 1212 cm⁻¹.

¹H-NMR (300 MHz, (D₆)DMSO) δ: 10.96 (d, J=4.9, 1H, NH-L-Biq); 8.38-8.28 (m, 3H NH-L-1-Ile [1]), NH-L-Ile [2], H—C(8')); 7.65-7.48 (m, 3H H—C (5'), H—C (6'), H—C (7'); 6.72 (s, 1H, olefinic H); 5.61-5.56 (m, 1H, H—C(3')); 4.39 (t, J=8.1, 1H, CH₁-L-Ile [2]); 4.16 (t, J=7.1, 1H, CHa-L-

Ile [1]); 3.59 (s, 3H, CO$_2$Me); 1.86-1.68 (m, 2H, CH-L-Ile [1], CH$_\beta$-L-Ile [2]); 1.54-0.98 (m, 7H, [Me-CH-Et] of L-Biq, [Me-CH—CH$_2$CH$_3$] of L-Biq, CH$_2$-L-Ile [1], CH$_2$-L-Ile [2]); 0.86-0.65 (m, 18H, [Me-CH—CH$_2$CH$_3$] of L-Biq, [Me-CH—CH$_2$CH$_3$] of L-Biq, [CH—CH$_3$] of L-Ile [1], [CH—CH$_3$] of L-Ile [2], [CH$_2$—CH$_3$] of L-Ile [1] [CH$_2$—CH$_3$] of L-Ile [2]).

$^{13}$C-NMR (50 MHz, (D$_6$)DMSO) δ: 189.2 (CSNH); 171.7, 171.3 (CO$_2$Me, CONH-L-Ile [2]); 164.5 (=C—CONH); 142.9 (C(4')), 132.8, 130.9, 123.8 (C(5'), C(6'), C(7')); 131.4 (C(8')); 130.6 (C(8a')); 129.4 (C(4a')); 121.5 (olefinic CH); 56.5 (CH$_\alpha$-L-Ile [2]); 56.1 (CH$_\alpha$-L-Ile [1]); 55.0 (C(3')); 51.5 (CO$_2$Me); 40.3, 36.8, 35.9 [Me-CH-Et] of L-Biq, CH$_\beta$-L-Ile [1], CH-L-Ile [2]); 24.9, 24.7, 24.2 ([Me-CH—CH$_2$CH$_3$] of L-Biq, CH$_2$-L-Ile [1], CH$_2$-L-Ile [2]); 15.3, 15.1, 14.7, 11.1, 10.8 (6 C [Me-CH—CH$_2$CH$_3$] of L-Biq, [Me-CH—CH$_2$CH$_3$] of L-Biq, [CH—CH$_3$] of L-Ile [1], [CH—CH$_3$] of L-Ile [2], [CH$_2$—CH$_3$] of L-Ile [1], [CH$_2$—CH$_3$] of L-Ile [2]).

MS (ES$^+$) m/e: 516 ([M+H]$^+$), 583 ([M+Na]$^+$), 1031 ([2M+H]$^+$), 1053 ([2M+Na]$^+$).

Example 33

Enzyme Activity Test: Inhibition of Calpain

The calpain inhibition capacity has been quantified in terms of the value of IC$_{50}$, which is defined as the concentration of inhibitor that reduces the catalytic activity of an enzyme by half. The lower the value of IC$_{50}$, the more powerful the inhibitor. Inhibition results on calpain I (the most relevant from a physiological point of view) of some compounds of the present invention are shown in table 1 and in FIG. 1.

TABLE 1

Representative results on the inhibition of calpain by compounds forming the object of this invention.

| Compounds | IC$_{50}$ |
|---|---|
| 7 | 25 nM |
| 11 | 124 μM |
| 12 | 85 μM |
| 13 | 59 μM |
| 14 | 5 μM |
| 15 | 140 μM |
| 16 | 130 μM |
| 17 | 86 nM |
| 18 | 742 nM |
| 19 | 100 μM |
| 20 | 48 μM |
| 21 | 5 μM |
| 22 | 17 μM |
| 23 | 7 μM |
| 24 | 50 μM |
| 25 | 447 nM |
| 26 | 159 nM |
| 27 | 626 nM |
| 28 | 38 μM |

The experiments were conducted spectrofluorimetrically using a Spectrofluor Tecan Corp 93382 spectrofluorimeter, exciting at 485 nM and measuring at 530 nM. Casein marked with BODIPY-FL® (Molecular Probes) was used as substrate and calpain I from porcine erythrocyte (Calbiochem, Cat No 208712) was used as enzyme. The freeze-dried substrate is component A of the protease assay kit EnzChek® green fluorescence from Molecular Probes (reference # E-6638); component B, known as 20× digestion buffer, contains 13 mL of 200 mM Tris-HCl, pH 7.8 and 2 mM sodium azide. The commercial calpain I that was used has a concentration of 1 mg in 1 mL of aqueous solution (the solution is 20 mM imidazol-HCl, pH 6.8, 1 mM EDTA, 1 mM EGTA, 5 mM β-mercaptoethanol, containing 30% glycerine).

Preparation of the Digestion Buffer Solution (Digestion Solution).

2.5 mL of 20× digestion buffer (component B of the kit from Molecular Probes) was diluted with water to a total volume of 50 mL.

Preparation of the Substrate Solution (Casein Solution).

200 μg of freeze-dried substrate (component A of the kit from *Molecular Probes*) was dissolved in 200 μL of phosphate saline buffer. This solution was decanted into a graduated flask and diluted with the digestion solution to a total volume of 40 mL.

Preparation of the Calpain Solution (Calpain Solution).

20 μL of commercial solution of calpain was diluted with the digestion solution to a total volume of 200 μL.

Preparation of the Inhibitor Solution (Inhibitor Solution).

The inhibitor was dissolved in DMSO. Each inhibitor was assayed at 7 different concentrations between 10 nM and 200 μM.

Enzyme Activity Experiments

All the data were obtained measuring the variation in fluorescence with time. The use of a multi-cell device and Eppendorf multi-channel pipettes permitted measurement of the variation in fluorescence in up to 64 experiments. In this way, the control experiment and the experiments with the different concentrations of inhibitor was carried out in the same set of measurements. All the experiments were conducted twice.

Control Experiment

The control experiment was carried out mixing 180 μL of casein solution and 5 μL of calpain solution. The reaction was initiated by the addition of 10 μL of a 50 μM solution of CaCl$_2$ in water, and the fluorescence was measured from the moment of the addition of Ca$^{2+}$ (time=0) and for 250-300 seconds (measuring during 20 kinetic cycles). The variation in fluorescence (ΔF) was represented against time (t). In order to test the effect of DMSO on enzyme activity, additional control experiments were conducted adding DMSO (in the quantities used in the experiments with the inhibitors), with the same result being obtained as in the control experiment.

Enzyme Activity in the Presence of Inhibitors

180 μL of casein solution, 5 μL of calpain solution and 5 μL of inhibitor solution (of variable concentration) were mixed together. The reaction was initiated by the addition of 10 μL of a 50 μM solution of CaCl$_2$ in water, and the fluorescence was measured from the moment of the addition of Ca$^{2+}$ (time=0) and for 250-300 seconds (measuring during 20 kinetic cycles). The variation in fluorescence (ΔF) was represented against time (t) and a value of ΔF/t was obtained for each experiment.

Determination of IC$_{50}$

For each inhibitor, the value of ΔF/t was represented against the concentration (c) of inhibitor, from c=0 up to c=200 μM. The data was fitted to a straight line and from the equation the value of IC$_{50}$ is determined (as the concentration of inhibitor causing the enzyme to have half the activity).

Abbreviations

Stated below are the meaning of the abbreviations used:
CANP: Calcium activated neutral protease
DMF: N,N-Dimethylformamide
DMSO: Dimethylsulphoxide
EA: Element analysis
EDTA: Ethylenediaminetetraacetic acid
EGTA: Ethylene-bis-(oxyethylenenitrile)tetraacetic acid
EtOAc: Ethyl acetate
ES: Electro-spray MS: Mass spectrum
IR: Infrared
m.p.: melting point
NMDA: N-methyl-D-aspartate
THF: Tetrahydrofuran
tlc: thin layer chromatography
Tris: Tris(hydroxymethyl)aminomethane
$^1$H-NMR: Proton nuclear magnetic resonance
$^{13}$C-NMR: Carbon-13 nuclear magnetic resonance

The invention claimed is:

1. A compound having a partially-reduced isoquinoline structure with substitution of a sec-butyl group in position 3, and of formula I or II,

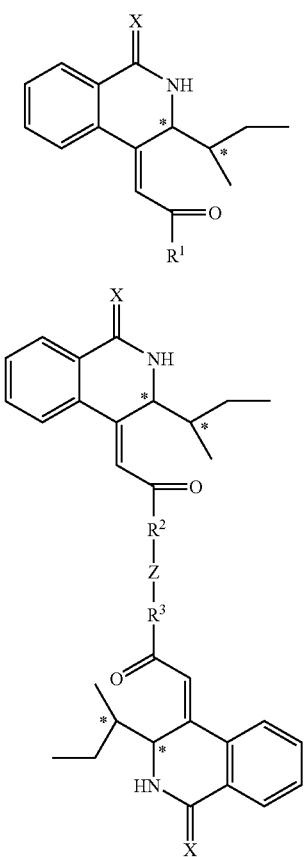

in which:
the group X is oxygen (O) or sulphur (S), indifferently,
the asterisk (*) represents a stereogenic centre, of configuration (R) or (S), indifferently,
the group $R^1$ is independently selected from the group consisting of:
  $NH_2$,
  $NHR^4$ in which $R^4$ represents an alkyl group, aryl group, an amino acid derivative or a peptide derivative,
  $NR^5R^6$ in which $R^5$ and $R^6$ are independently selected from among an alkyl group, aryl group, an amino acid derivative, a peptide derivative, and groups $R^5$ and $R^6$ forming a cyclic system,
  OH,
  $OR^7$ in which $R^7$ represents an alkyl or aryl group;
the groups $R^2$ and $R^3$ are the same or different and are independently selected from among the groups O (oxygen), NH or $NR^8$ in which $R^8$ represents an alkyl or aryl group Z is selected from among the groups,
  alkyl with between 2 and 8 carbon atoms,
  aryl,
  arylalkyl,
  oxyalkyl chain independently containing between 1 and 3 atoms of oxygen and between 2 and 10 atoms of carbon,
  fragment derived from amino acid or peptide.

2. A compound according to claim 1, said compound is selected from among:
methyl (S,S,Z)-(3-sec-butyl-1-oxo-2,3-dihydro-1H-isoquinolin-4-yliden)-acetate (7),
(S,S,Z)-(3-sec-butyl-1-oxo-2,3-dihydro-1H-isoquinolin-4-yliden)-acetic acid (8),
iso-propyl (S,S,Z)-(3-sec-butyl-1-oxo-2,3-dihydro-1H-isoquinolin-4-yliden) -acetate (9),
1-butyl (S,S,Z)-(3-sec-butyl-1-oxo-2,3-dihydro-1H-isoquinolin-4-yliden)-acetate (10),
benzyl (S,S,Z)-(3-sec-butyl-1-oxo-2,3-dihydro-1H-isoquinolin-4-yliden)-acetate (11),
(S,S,S,S,Z,Z Z)-(3-sec-butyl-1-oxo-2,3-dihydro-1H-isoquinolin-4-yliden)-but-2-enyl 4-[2-3-sec-butyl-1-oxo-2,3-dihydro-1H-isoquinolin-4-yliden)-acetoxyl]-acetate (12),
(S,S,S,S,Z,Z)-(3-sec-butyl-1-oxo-2,3-dihydro-1H-isoquinolin-4-yliden)-but 2-inyl 4-[2-3-sec-butyl-1-oxo-2,3-dihydro-1H-isoquinolin-4-yliden)-acetoxyl]-acetate (13),
(S,S,S,S,Z,Z)-4-[2-(3-sec-butyl-1-oxo-2,3-dihydro-1H-isoquinolin-4-yliden) -acetoxyl]-benzyl (3-sec-butyl-1-oxo-2,3-dihydro-1H-isoquinolin-4-yliden) -acetate (14),
(S,S,Z)-N-benzyl-2-(3-sec-butyl-1-oxo-2,3-dihydro-1H-isoquinolin-4-yliden)-acetamide (15),
(S,S,Z)-N-(3-acetyl-phenyl)-2-(3-sec-butyl-1-oxo-2,3-dihydro-1H-isoquinolin -4-yliden)-acetamide (16),
(S,S,Z)-N-(2'-amino-biphenyl-2-yl)-2-(3-sec-butyl-1-oxo-2,3-dihydro-1H-isoquinolin -4-yliden)-acetamide (17),
(S,S,S,S,Z,Z)-2,2'-bis-[(3-sec-butyl-1-oxo-2,3-dihydro-1H-isoquinolin-4-yliden) -acetylamino]biphenyl (18),
(S,S,S,Z)-9H-fuorene-9-ylmethyl (1- {2'-[2-(3-sec-butyl-1-oxo-2,3-dihydro 1H-isoquinolin-4-yliden)-acetylamino]-biphenyl-2-ylcarbamoyl}-2-methyl -propyl)-carbamate (19),
(S,S,S,Z)-9H-fuorene-9-ylmethyl (1-{2'-[2-(3-sec-butyl-1-oxo-2,3-dihydro -1H-isoquinolin-4-yliden)-acetylamino]-biphenyl-2-ylcarbamoyl}-2-phenyl -ethyl)-carbamate (20),
(S,S,S,S,Z)-9H-fuorene-9-ylmethyl (1-{2'-[2-(3-sec-butyl-1-oxo-2,3-dihydro -1H-isoquinolin-4-yliden)-acetylamino]-biphenyl-2-ylcarbamoyl}-2-methyl-butyl) -carbamate (21),
(S,S,S,Z)-2-amino-N-{2'-[2-(3-sec-butyl-1-oxo-2,3-dihydro-1H-isoquinolin 4-yliden)-acetylamino]-biphenyl-2-yl}-3-methyl-butyramide (22),
(S,S,S,Z)-2-amino-N-{2'-[2-(3-sec-butyl-1-oxo-2,3-dihydro- 1H-isoquinolin -4-yliden)-acetylamino]-biphenyl-2-yl}-3-phenyl-propionamide (23),
(S,S,S,S,Z)-2-amino-N-{2'-[2-(3-sec-butyl-1-oxo-2,3-dihydro-1H-isoquinolin -4-yliden)-acetylamino]-biphenyl-2-yl}-3-methyl-pentanamide (24), methyl (S,S,S,S,S,S,Z)-2-{2-[2-(3-sec-butyl-1-oxo-2,3-dihydro-1H-isoquinolin-4-yliden)-acetylamino]-3-methyl-pentanoylamino}-3-methyl-pentanoate (25), methyl (S,S,S,S,S,S,S,Z)-2-(2-{[2-(3-sec-butyl-1-oxo-2,3-dihydro-1H isoquinolin-4-yliden)-acetylamino]1-3-methyl-pentanoylamino}-3-methyl -pentanoylamino)-3-methyl-pentanoate (26), methyl (S,S,S,S,Z)-2-{2[2(3-sec-butyl-1-oxo-2,3-dihydro-1H-isoquinolin -4-yliden)-acetylamino]-3-methyl-butirylamino}-3-phenyl-propionate (27), methyl (S,S,Z)-(3-sec-butyl-1-thioxo-2,3-dihydro-1H-isoquinolin-4-yliden) -acetate (28), (S,S,Z)-(3-sec-butyl-1-thioxo-2,3-dihydro-1H-isoquinolin-4-yliden)-acetic acid (29), and methyl (S,S,S,S,S,Z)-2- {2-[2-(3-sec-butyl-1-thioxo-2,3-dihydro-1H-isoquinolin-4-yliden)-acetylamino]-3-methyl-pentanoylamino}-3-methyl-pentanoate (30), and any of their isomers.

3. A method of synthesis for the compounds of formula I or II, defined in claim 1, said method comprising transforming an intermediate compound, which is any isomer of (3-sec-butyl-1-oxo-2,3-dihydro-1H-isoquinolin-4-yliden)-acetic acid, into amide or ester.

4. A method of synthesis for the compounds of formula I or II, defined in claim 1, wherein an intermediate compound, which is any isomer of (3-sec-butyl-1-oxo-2,3-dihydro-1H-isoquinolin -4-yliden)-methyl acetate, is transformed by hydrolysis.

5. A method of synthesis for the compounds of formula I or II, defined in claim 1, wherein an intermediate compound, which is any isomer of methyl 4-(2-iodobenzoylamino)-5-methyl-2-heptenoate, is transformed into a derivative of isoquinoline.

6. A method of synthesis for the compounds of formula I or II, defined in claim 1, wherein an intermediate compound, which is any isomer of N-[(1-hydroxymethyl-2-methyl)-butyl]-2-iodo-benzamide, is transformed into an α,β-unsaturated ester.

7. A method of synthesis for the compounds of formula I or II, defined in claim 1, wherein an intermediate compound, which is any isomer of methyl 2-(2-iodobenzoylamino)-3-methyl -pentanoate, is reduced to alcohol.

8. Method of inhibiting calpain in a patient which comprises administering to such patient a compound as defined in claim 1, having a partially-reduced isoquinoline structure with substitution of a sec-butyl group in position 3, and of formula I or II,

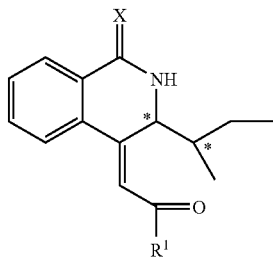

I

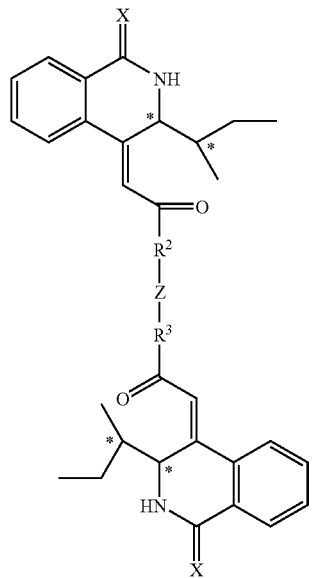

II in which:
the group X is oxygen (O) or sulphur (S), indifferently,
the asterisk (*) represents a stereogenic centre, of configuration (R) or (S), indifferently,
the group $R^1$ is independently selected from the group consisting of:
$NH_2$,
$NHR^4$ in which $R^4$ represents an alkyl group, aryl group, an amino acid derivative or a peptide derivative,
$NR^5R^6$ in which $R^5$ and $R^6$ are independently selected from among an alkyl group, aryl group, an amino acid derivative, a peptide derivative, and groups $R^5$ and $R^6$ forming a cyclic system,
OH,
$OR_7$ in which $R^7$ represents an alkyl or aryl group;
the groups $R^2$ and $R^3$ are the same or different and are independently selected from among the groups O (oxygen), NH or $NR^8$ in which $R^8$ represents an alkyl or aryl group
Z is selected from among the groups,
alkyl with between 2 and 8 carbon atoms,
aryl,
arylalkyl,
oxyalkyl chain independently containing between 1 and 3 atoms of oxygen and between 2 and 10 atoms of carbon,
fragment derived from amino acid or peptide, as caplain inhibitor for the treatment of a degenerative disease, wherein the degenerative disease is cerebral ischemia, cardiac ischaemia, cerebral ictus, Alzheimer's, Parkinson's, Huntington's, muscular dystrophy, cataracts or demyelinating diseases.

9. Method according to claim 8, wherein said compound is a compound of formula I or II and selected from among:
methyl (S,S,Z)-(3-sec-butyl-1-oxo-2,3-dihydro-1H-isoquinolin-4-yliden)-acetate (7),
benzyl (S,S,Z)-(3- sec-butyl-1-oxo-2,3-dihydro-1H-isoquinolin-4-yliden)-acetate (11),
(S,S,S,S,Z,Z,Z)-(3-sec-butyl-1-oxo-2,3-dihydro-1H-isoquinolin-4-yliden)-but -2-enyl 4-[2-3-sec-butyl-1-oxo-2,3-dihydro-1H-isoquinolin-4-yliden)-acetoxyl ]-acetate (12), (S,S,S,S,Z,Z)-(3-sec-butyl-1-oxo-2,3-dihydro-1H-isoquinolin-4-yliden)-but-2-inyl 4-[2-3-sec-butyl-1-oxo-2,3-dihydro-1H-isoquinolin-4-yliden) -acetoxyl]-acetate (13), (S,S,S,S,Z,Z)-4-[2-(3-sec-butyl-1-oxo-2,3-dihydro-1H-isoquinolin-4-yliden) -acetoxyl]-benzyl (3-sec-butyl-1-oxo-2,3-dihydro-1H-isoquinolin-4-yliden) -acetate (14), (S,S,Z)-N-benzyl-2-(3-sec-butyl-1-oxo-2,3-dihydro-1H-isoquinolin-4-yliden) -acetamide (15), (S,S,Z)-N-(3-acetyl-phenyl)-2-(3-sec-butyl-1-oxo-2,3-dihydro-1H-isoquinolin -4-yliden)-acetamide (16), (S,S,Z)-N-(2'-amino-biphenyl-2-yl)-2-(3-sec-butyl-1-oxo-2,3-dihydro-1H-isoquinolin -4-yliden)-acetamide (17), S,S,S,S,Z,Z)-2,2'-bis-[(3-sec-butyl-1-oxo-2,3-dihydro-1H-isoquinolin-4-yliden) -acetylamino]biphenyl (18), (S,S,S,Z)-9H-fuorene-9-ylmethyl (1-{2'-[2-(3-sec-butyl-1-oxo-2,3-dihydro -1H-isoquinolin-4-yliden)-acetylamino]-biphenyl-2-ylcarbamoyl}-2- methyl-propyl) -carbamate (19), (S,S,S,Z)-9H-fuorene-9-ylmethyl (1-{2'-[2-(3-sec-butyl-1-oxo-2,3-dihydro -1H-isoquinolin-4-yliden)-acetylamino]-biphenyl-2-ylcarbamoyl}-2-phenyl -ethyl)-carbamate (20), (S,S,S,S,Z)-9H-fuorene-9-ylmethyl (1-{2'-[2-(3-sec-butyl-1-oxo-2,3-dihydro -1H-isoquinolin-4-yliden)-acetylamino]-biphenyl-2-ylcarbamoyl}-2-methyl -butyl)-carbamate (21), (S,S,S,Z)-2-amino-N-{2'-[2-(3-sec-butyl-1-oxo-2,3-dihydro-1H-isoquinolin -4-yliden)-acetylamino]-biphenyl-2-yl}-3-methyl-butyramide (22), (S,S,S,Z)-2-amino-N-{2'-[2-(3-sec-butyl-1-oxo-2,3-dihydro-1H-isoquinolin -4-yliden)-acetylamino]-biphenyl-2-yl}-3-phenyl-propionamide (23), (S,S,S,S,Z)-2-amino-N-{2'-[2-(3-sec-butyl-1-oxo-2,3-dihydro-1H-isoquinolin -4-yliden)-acetylamino]-biphenyl-2-yl}-3-methyl-pentanamide (24), methyl (S,S,S,S,S,S,Z)-2-{2[2-(3-sec-butyl-1-oxo-2,3-dihydro-1H-soquinolin -4-yliden)-acetylamino]-3-methyl-pentanoylamino}-3-methyl-pentanoate (25), methyl (S,S,S,S,S,S,S,S,Z)-2-(2-{2-[2-(3-sec-butyl-1-oxo-2,3-dihydro-1H -isoquinolin-4-yliden)-acetylamino]-3-methyl-pentanoylamino}-3-methyl-pentanoylamino) -3-methyl-pentanoate (26), methyl (S,S,S,S,Z)-2-{2-[2-(3-sec-butyl-1-oxo-2,3-dihydro-1H-isoquinolin -4-yliden)-acetylamino]-3-methyl-butirylamino}-3-phenyl-propionate (27), and methyl (S,S,Z)-(3-sec-butyl-1-thioxo-2,3-dihydro-1H-isoquinolin-4-yliden)-acetate (28), as calpain inhibitor.

10. Method according to claim 8, in which the demyelinating degenerative disease is multiple sclerosis.

* * * * *